United States Patent
Hafner et al.

(10) Patent No.: US 9,567,351 B2
(45) Date of Patent: Feb. 14, 2017

(54) HETEROPHASIC COPOLYMERS

(75) Inventors: Norbert Hafner, Linz (AT); Luigi Resconi, Ferrara (IT); Markus Gahleitner, Neuhofen/Krems (AT); Jimgbo Wang, Linz (AT); Pascal Castro, Helsinki (FI); Pavel Sergeevich Kulyabin, Moscow (RU); Vyatcheslav Izmer, Moscow (RU); Alexander Voskoboynikov, Moscow (RU); Dmitry Kononovich, Moscow (RU); Ville Virkkunen, Helsinki (FI)

(73) Assignee: BOREALIS AG, Vienna (AT)

( * ) Notice: Subject to any disclaimer, the term of this patent is extended or adjusted under 35 U.S.C. 154(b) by 0 days.

(21) Appl. No.: 14/131,549

(22) PCT Filed: Jul. 6, 2012

(86) PCT No.: PCT/EP2012/063332
§ 371 (c)(1),
(2), (4) Date: Mar. 24, 2014

(87) PCT Pub. No.: WO2013/007664
PCT Pub. Date: Jan. 17, 2013

(65) Prior Publication Data
US 2014/0206819 A1    Jul. 24, 2014

(30) Foreign Application Priority Data
Jul. 8, 2011 (EP) .................................. 11173344

(51) Int. Cl.
| C08L 23/00 | (2006.01) |
| C07F 7/08 | (2006.01) |
| C07C 13/465 | (2006.01) |
| C07F 17/00 | (2006.01) |
| C08L 23/12 | (2006.01) |
| C08F 4/6592 | (2006.01) |
| C08F 10/06 | (2006.01) |
| C08F 110/06 | (2006.01) |
| C08F 210/06 | (2006.01) |
| C08F 4/659 | (2006.01) |

(52) U.S. Cl.
CPC .......... *C07F 7/0818* (2013.01); *C07C 13/465* (2013.01); *C07F 17/00* (2013.01); *C08F 4/65927* (2013.01); *C08F 10/06* (2013.01); *C08L 23/12* (2013.01); *C08F 4/65912* (2013.01); *C08F 4/65916* (2013.01); *C08F 110/06* (2013.01); *C08F 210/06* (2013.01); *C08L 2207/02* (2013.01); *C08L 2314/06* (2013.01)

(58) Field of Classification Search
CPC .......................... C08F 4/65927; C07F 7/0818
See application file for complete search history.

(56) References Cited

U.S. PATENT DOCUMENTS

| 5,360,849 A * | 11/1994 | Braga et al. ............... 524/68 |
| 5,753,773 A | 5/1998 | Langhauser et al. |
| 6,943,215 B2 * | 9/2005 | Stevens et al. ............. 525/191 |
| 2003/0149199 A1 | 8/2003 | Schottek et al. |
| 2003/0195299 A1 | 10/2003 | Stevens et al. |
| 2005/0075458 A1 * | 4/2005 | Salek et al. ............... 525/240 |
| 2006/0020096 A1 | 1/2006 | Schottek et al. |
| 2010/0160564 A1 * | 6/2010 | Kameo ..................... 525/190 |

FOREIGN PATENT DOCUMENTS

| CN | 101747556 A | 6/2010 |
| EP | 0834519 A1 | 4/1998 |
| EP | 1074577 A1 | 2/2001 |
| EP | 2053086 A1 | 4/2009 |
| EP | 2072546 A1 | 6/2009 |
| EP | 2075284 A1 | 7/2009 |
| EP | 2426171 A1 | 3/2012 |
| WO | 0148034 A2 | 7/2001 |
| WO | 03045551 A1 | 6/2003 |
| WO | 03106553 A1 | 12/2003 |
| WO | 2004106351 A1 | 12/2004 |

OTHER PUBLICATIONS

International Search Report and written opinion mailed Oct. 9, 2012 (PCT/EP2012/063332); ISA/EP.
Grein et al., Melt viscosity effects in Ethylene-Propylene Copolymers, Rheol.Acta, 46 (2007) 1083-1089.
Grein et al., Impact modified isotatic polypropylene with controlled rubber intrinsic viscosities: some new aspects about morphology and fracture; Journal of Applied Polymer Science, vol. 87, 1702-1712 (2003).
Spaleck et al., Journal of Molecular catalysis A, 1998, vol. 128, p. 279.
Miyake et al, Macromolecules 1995, vol. 28, p. 3074.
Elder et al., Kin. Cat. 2006, vol. 47(2), p. 192.

* cited by examiner

*Primary Examiner* — Irina Krylova
(74) *Attorney, Agent, or Firm* — Banner & Witcoff, Ltd.

(57) ABSTRACT

A heterophasic polypropylene resin comprising a polypropylene homopolymer matrix phase (A) and an ethylene-propylene copolymer phase (B) dispersed within the matrix, wherein the xylene soluble fraction of the heterophasic polypropylene resin is in the range 20 to less than 50 wt %; the heterophasic polypropylene resin has an MFR2 of 0.01 to 50 g/10 min; the ethylene content of the xylene soluble fraction of the heterophasic polypropylene resin is in the range of at least 20 wt % to less than 50 wt %; the heterophasic polypropylene resin has a notched charpy impact strength at −20 C of at least 25 kJ/m$^2$, preferably at least 50 kJ/m$^2$; and wherein the MFR$_2$ (Matrix)/MFR$_2$ (XS)≥5, preferably ≥10.

8 Claims, 1 Drawing Sheet

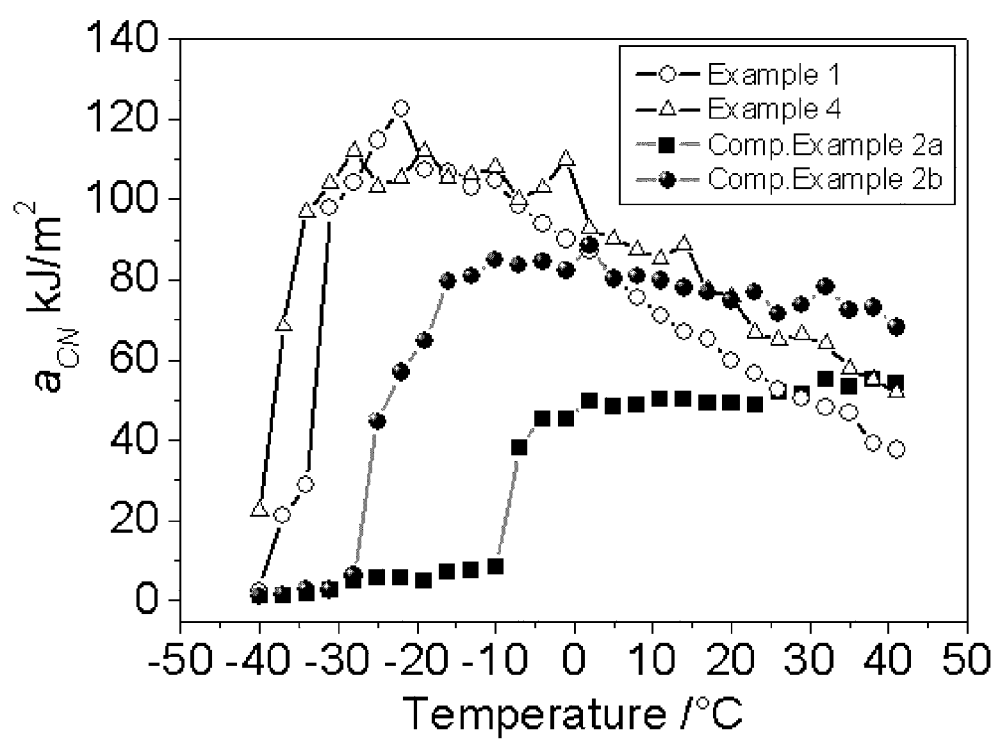

HETEROPHASIC COPOLYMERS

The present application is a U.S. National Phase filing of International Application No. PCT/EP2012/063332, filed on Jul. 6, 2012, designating the United States of America and claiming priority to European patent application No. 11173344.0, filed Jul. 8, 2011, and this application claims priority to and the benefit of the above-identified applications, which are both incorporated by reference herein in their entireties.

This invention relates to new heterophasic polypropylene resins comprising a propylene homopolymer matrix and an ethylene-propylene copolymer phase dispersed within the matrix with excellent low temperature impact properties. Further, it relates to a process for producing such a polypropylene resin and the use of such a resin for the production of an article and in the formation of polymer blends. The heterophasic polypropylene resins of the invention are obtainable using certain new asymmetrical bisindenyl metallocene catalysts. In particular, aspects of the invention relate to heterophasic polypropylene resins comprising at least 20 wt % of the ethylene propylene rubber phase in which the ethylene propylene rubber phase has an ethylene content of at least 20 wt %. These resins exhibit remarkable mechanical properties, especially impact strength at low temperature.

The glass transition temperature of crystalline isotactic polypropylene (iPP) of around 0° C. limits the applicability of all iPP-based materials in the sub-zero temperature range. Combining iPP as a matrix phase with an elastomeric component having a sufficiently low glass transition temperature (Tg) is a standard approach for overcoming this problem. Even then, however, the performance at temperatures below around −10° C. is often limited.

One reason for this is the problem of dispersion of the elastomeric component in the matrix, due in part to the particle size of the elastomeric phase. Problems can also arise due to the viscosity ratio between elastomeric component and matrix (PP) phase, and the compatibility between these two phases. Incompatibility is a result of the compositional differences between the materials.

Good compatibility is often achieved at high propylene (C3) content (and hence low ethylene (C2) content) in the rubber phase which, however, leads to a higher Tg, again limiting the performance at very low temperatures, such as below −10° C.

The interrelations governing compatibility and phase structure development have been analyzed in C. Grein, M. Gahleitner, B. Knogler & S. Nestelberger, Melt viscosity effects in Ethylene-Propylene Copolymers, Rheol. Acta, 46 (2007) 1083-1089. Generally, a higher intrinsic viscosity for the xylene soluble phase leads to tougher blends.

It is therefore of interest to develop ethylene/propylene impact copolymers having different relations between composition and mechanical performance. The use of certain single-site catalysts (SSC) have been found to be a suitable means for achieving this target.

Metallocene catalysts have been used to manufacture polyolefins for many years. Countless academic and patent publications describe the use of these catalysts in olefin polymerisation. Metallocenes are now used industrially and polyethylenes and polypropylenes in particular are often produced using cyclopentadienyl based catalyst systems with different substitution patterns.

The present inventors sought new metallocenes to enable the formation of the heterophasic copolymer resins of the invention. In particular, the inventors sought a way of engineering a significant molecular weight difference between the two components. This difference is believed to contribute to good impact properties.

The present inventors have found a new class of asymmetric, chiral, racemic, anti, bridged bisindenyl metallocenes which are simple to synthesize despite their asymmetry and which are readily separable from their syn (meso-like) isomers. The two indenyl ligands are different from each other, that is, each indenyl ligand bears a set of substituents that are either chemically different, or located in different positions with respect to the other indenyl ligand. For the purpose of this invention, anti means that the two indenyl ligands are oriented in opposite directions with respect to the cyclopentadienyl-metal-cyclopentadienyl plane, while syn means that the two indenyl ligands are oriented in the same direction with respect to the cyclopentadienyl-metal-cyclopentadienyl plane.

The catalysts have high catalyst productivity and improved performance in the production of high molecular weight polypropylene homopolymers, especially those of $MFR_2<1$ and in the production of propylene copolymers. During copolymer manufacture, the metallocenes of certain examples possess reduced chain transfer to ethylene, enabling the production of high molecular weight heterophasic copolymers.

Asymmetrical metallocenes able to produce isotactic polypropylene have been described in the literature, such as for example in Spaleck et al., Journal of Molecular catalysis A, 1998, vol. 128, p. 279, or Miyake et al., Macromolecules 1995, vol. 28, p. 3074. The performance of these metallocenes was, however, far from satisfactory. New, asymmetric metallocenes have been described in the patent and scientific literature, for example EP-A-0834519, WO2001/048034, WO2003/045551, EP-A-1074577, and Elder et al., Kin. Cat. 2006, vol 47(2), p. 192. Here as well, the synthesis of the ligands is highly complicated and the performance of the catalysts not fully satisfactory, especially concerning either molecular weight or catalyst activity.

Our invention concerns the use of asymmetrical metallocenes in heterophasic propylene copolymer manufacture, especially the anti-isomers thereof, bearing as Π-ligands two indenyls which are different in their substitution pattern while still being relatively simple to synthesize, in particular where the 5 position of one ligand carries a hydrogen atom and the 5-position of the other ring is substituted by a non hydrogen group. These metallocenes have surprisingly been found to possess higher activities than previously reported asymmetric catalysts, as well as higher activities compared to their symmetrical analogues.

The inventors have therefore found that certain asymmetrical metallocene catalysts enable the formation of polymers with remarkable properties. In particular, some examples provide ethylene/propylene impact copolymers having more than 20 wt % (preferably more than 25 wt %) of an ethylene propylene rubber (EPR) component where the C3 content is higher than the C2 (i.e. C2(XS)<50 wt %) and a molecular weight significantly below that of the matrix (i.e. MFR(XS)/MFR(matrix) 2:5, preferably 2:10).

Heterophasic polypropylene copolymers are known. WO93/106553 describes propylene copolymer compositions with good low temperature impact properties. The polymers exemplified have low C2 content in the amorphous phase and poor impact performance at low temperature.

U.S. Pat. No. 5,753,773 describes multiphase block copolymers with good shape stability. The copolymer phase in these copolymers can contain anything from 2 to 98 wt % comonomer other than propylene.

EP-A-2072546 also covers heterophasic polypropylenes having very high ethylene content in the amorphous phase. Ethylene contents of 60 to 85 mol % are observed in the xylene soluble component.

EP-A-2053086 describes heterophasic copolymers typically made using Ziegler Natta catalysis for packaging. These polymers do not have a marked molecular weight difference between matrix and amorphous phases.

There is no teaching therefore of the heterophasic polymers claimed herein in which there is a marked difference in molecular weight between matrix and amorphous phases in the context of a heterophasic propylene copolymer comprising at least 20 wt % of the EPR phase. This combination of features leads to the remarkable impact properties observed in the examples.

SUMMARY

Thus, viewed from one aspect the invention provides a heterophasic polypropylene resin comprising a polypropylene homopolymer matrix phase (A) and an ethylene-propylene copolymer phase (B) dispersed within the matrix, wherein the xylene soluble fraction of the heterophasic polypropylene resin is in the range 20 to less than 50 wt %;

the heterophasic polypropylene resin has an $MFR_2$ of 0.01 to 50 g/10 min;

the ethylene content of the xylene soluble fraction of the heterophasic polypropylene resin is in the range of at least 20 wt % to less than 50 wt %;

the heterophasic polypropylene resin has a notched charpy impact strength at −20° C. of at least 25 $kJ/m^2$, preferably at least 50 $kJ/m^2$; and wherein the $MFR_2$ (XS)/$MFR_2$(matrix)≥5, preferably ≥10.

Alternatively viewed, the invention provides a heterophasic polypropylene resin comprising a polypropylene homopolymer phase (A) and an ethylene-propylene copolymer phase (B) dispersed within the phase (A), wherein the xylene soluble fraction of the heterophasic polypropylene resin is in the range 20 to less than 50 wt %;

the heterophasic polypropylene resin has an $MFR_2$ of 0.01 to 50 g/10 min;

the ethylene content of the xylene soluble fraction of the heterophasic polypropylene resin is in the range of at least 20 wt % to less than 50 wt %;

the heterophasic polypropylene resin has a notched charpy impact strength at −20° C. of at least 25 $kJ/m^2$, preferably at least 50 $kJ/m^2$; and wherein the $MFR_2$ (XS)/$MFR_2$ (xylene insoluble)≥5, preferably ≥10.

Alternatively viewed, the invention provides a heterophasic polypropylene resin comprising a polypropylene homopolymer matrix phase (A) and an ethylene-propylene copolymer phase (B) dispersed within the matrix, wherein the content of component (B) is in the range 20 to less than 50 wt % of the heterophasic polypropylene resin;

the heterophasic polypropylene resin has an $MFR_2$ of 0.01 to 50 g/10 min;

the ethylene content of the ethylene-propylene copolymer (B) is in the range of at least 20 wt % to less than 50 wt %;

the $MFR_2$ (Matrix) is 0.2 g/10 min or less; and wherein the $MFR_2$ (XS)/$MFR_2$(matrix)≥5, preferably ≥10.

Alternatively viewed, the invention provides a heterophasic polypropylene resin comprising a polypropylene homopolymer matrix phase (A) and an ethylene-propylene copolymer phase (B) dispersed within the matrix, wherein the xylene soluble fraction of the heterophasic polypropylene resin is in the range 20 to less than 50 wt %;

the heterophasic polypropylene resin has an $MFR_2$ of 0.01 to 50 g/10 min;

the ethylene content of the xylene soluble fraction of the heterophasic polypropylene resin is in the range of at least 20 wt % to less than 50 wt %;

the $MFR_2$ (Matrix) is 0.2 g/10 min or less; and wherein the $MFR_2$ (XS)/$MFR_2$(matrix)≥5, preferably ≥10.

Alternatively viewed, the invention provides a heterophasic polypropylene resin comprising a polypropylene homopolymer phase (A) and an ethylene-propylene copolymer phase (B) dispersed within phase (A), wherein the xylene soluble fraction of the heterophasic polypropylene resin is in the range 20 to less than 50 wt %;

the heterophasic polypropylene resin has an $MFR_2$ of 0.01 to 50 g/10 min;

the ethylene content of the xylene soluble fraction of the heterophasic polypropylene resin is in the range of at least 20 wt % to less than 50 wt %;

the $MFR_2$ (xylene insoluble) is 0.2 g/10 min or less; and wherein the $MFR_2$ (XS)/$MFR_2$ (xylene insoluble)≥5, preferably ≥10.

Viewed from another aspect the invention provides a process for the preparation of a heterophasic polypropylene resin as hereinbefore defined comprising:

(i) polymerising propylene only in a first stage; and (ii) polymerising at least ethylene and propylene in a second stage;

both stages being carried out in the presence of the same asymmetrical metallocene catalyst, preferably a racemic catalyst comprising a complex of formula (I)

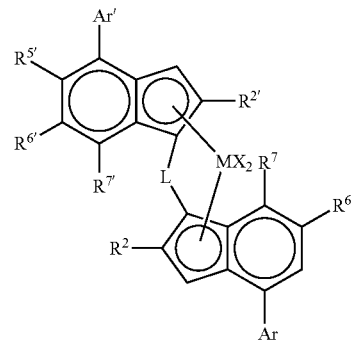

wherein

M is zirconium or hafnium;

each X is a sigma ligand;

L is a divalent bridge selected from —$R'_2C$—, —$R'_2C$—$CR'_2$—, —$R'_2Si$—, —$R'_2Si$—$SiR'_2$—, —$R'_2Ge$—, wherein each R' is independently a hydrogen atom, $C_1$-$C_{20}$-hydrocarbyl, tri($C_1$-$C_{20}$-alkyl)silyl, $C_6$-$C_{20}$-aryl, $C_7$-$C_{20}$-arylalkyl or $C_7$-$C_{20}$-alkylaryl;

$R^2$ and $R^{2'}$ are each independently a $C_1$-$C_{20}$ hydrocarbyl radical optionally containing one or more heteroatoms from groups 14-16;

$R^{5'}$ is a $C_{1-20}$ hydrocarbyl group optionally containing one or more heteroatoms from groups 14-16 and optionally substituted by one or more halo atoms;

$R^6$ and $R^{6'}$ are each independently hydrogen or a $C_{1-20}$ hydrocarbyl group optionally containing one or more heteroatoms from groups 14-16;

$R^7$ and $R^{7'}$ are each independently hydrogen or $C_{1-20}$ hydrocarbyl group optionally containing one or more heteroatoms from groups 14-16;

Ar is independently an aryl or heteroaryl group having up to 20 carbon atoms optionally substituted by one or more groups $R^1$;

Ar' is independently an aryl or heteroaryl group having up to 20 carbon atoms optionally substituted by one or more groups $R^1$;

each $R^1$ is a $C_{1-20}$ hydrocarbyl group or two $R^1$ groups on adjacent carbon atoms taken together can form a fused 5 or 6 membered non aromatic ring with the Ar group, said ring being itself optionally substituted with one or more groups $R^4$; and each $R^4$ is a $C_{1-20}$ hydrocarbyl group; and (ii) a cocatalyst comprising a compound of a group 13 metal, e.g. Al or boron.

The catalyst may be used in non-supported form or in solid form. The catalyst may be used as a homogeneous catalyst or heterogeneous catalyst.

The catalyst of certain examples in solid form, preferably in solid particulate form can be either supported on an external carrier material, like silica or alumina, or, in a particularly preferred embodiment, is free from an external carrier, however still being in solid form. For example, the solid catalyst is obtainable by a process in which (a) a liquid/liquid emulsion system is formed, said liquid/liquid emulsion system comprising a solution of the catalyst components (i) and (ii) dispersed in a solvent so as to form dispersed droplets; and (b) solid particles are formed by solidifying said dispersed droplets.

Viewed from another aspect the invention provides a polymer blend comprising a heterophasic polypropylene resin as hereinbefore defined and a second different polyolefin, e.g. 5 and 50 wt % of the inventive heterophasic polypropylene resin will be added to another polypropylene resin having a higher $MFR_2$ than the inventive heterophasic polypropylene resin.

Viewed from another aspect the invention provides the use of a heterophasic polypropylene resin as hereinbefore defined in the manufacture of an article such as a flexible tube, pipe, profile, cable insulation, sheet or film.

DEFINITIONS

Throughout the description the following definitions are employed.

The copolymer of some examples is a heterophasic polypropylene resin. This means that the polymer contains a crystalline or semi-crystalline propylene homopolymer component (A) and an amorphous ethylene propylene rubber component (B). The two components are mixed together and as there is an excess of the (A) component, it can be considered that the (B) component is dispersed in the (A) component.

By free from an external carrier is meant that the catalyst does not contain an external support, such as an inorganic support, for example, silica or alumina, or an organic polymeric support material.

The term $C_{1-20}$ hydrocarbyl group therefore includes $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl groups, $C_{7-20}$ alkylaryl groups or $C_{7-20}$ arylalkyl groups or of course mixtures of these groups such as cycloalkyl substituted by alkyl. Linear and branched hydrocarbyl groups cannot contain cyclic units. Aliphatic hydrocarbyl groups cannot contain aryl rings.

Unless otherwise stated, preferred $C_{1-20}$ hydrocarbyl groups are $C_{1-20}$ alkyl, $C_{4-20}$ cycloalkyl, $C_{5-20}$ cycloalkylalkyl groups, $C_{7-20}$ alkylaryl groups, $C_{7-20}$ arylalkyl groups or $C_{6-20}$ aryl groups, especially $C_{1-10}$ alkyl groups, $C_{6-10}$ aryl groups, or $C_{7-12}$ arylalkyl groups, e.g. $C_{1-8}$ alkyl groups. Most especially preferred hydrocarbyl groups are methyl, ethyl, propyl, isopropyl, tertbutyl, isobutyl, $C_{5-6}$-cycloalkyl, cyclohexylmethyl, phenyl or benzyl.

The term halo includes fluoro, chloro, bromo and iodo groups, especially chloro groups, when relating to the complex definition.

The oxidation state of the metal ion is governed primarily by the nature of the metal ion in question and the stability of the individual oxidation states of each metal ion.

It will be appreciated that in the complexes of the invention, the metal ion M is coordinated by ligands X so as to satisfy the valency of the metal ion and to fill its available coordination sites. The nature of these σ-ligands can vary greatly.

Catalyst activity is defined in this application to be the amount of polymer produced/g catalyst/h. Catalyst metal activity is defined here to be the amount of polymer produced/g Metal/h. The term productivity is also sometimes used to indicate the catalyst activity although herein it designates the amount of polymer produced per unit weight of catalyst.

The term EPR or ethylene propylene rubber/ethylene propylene copolymer is used here in the context of component (B) of the heterophasic polypropylene resin. EPR's of some examples have a larger propylene content than ethylene content.

DETAILED DESCRIPTION

Polymer Properties

This invention primarily relates to a heterophasic polypropylene resin comprising a polypropylene homopolymer phase (A) and an ethylene-propylene copolymer phase (B) dispersed within the phase (A).

It has surprisingly been found that a heterophasic polypropylene resin with the characteristics above shows excellent impact properties especially at low temperatures. Without wishing to be limited by theory, this is believed to be due to the relationship between the molecular weight (in terms of MFR) between the matrix and elastomeric components in the context of the relative amounts of these components mentioned above.

It is possible for the EPR component (B) to contain comonomers other than ethylene and propylene such as other for example $C_{4-20}$ olefins, e.g. 1-butene, 1-hexene, 4-methyl-1-pentene, 1-octene etc. However, it is preferred if no other comonomers are present.

The polymers of the invention preferably comprise an isotactic propylene matrix component (A). Component (A) may consist of a single propylene homopolymer but (A) may also comprise a mixture of different propylene homopolymers. Ideally, however a single propylene homopolymer is present.

The same applies for component (B): it may consist of a single polymer, but may also comprise a mixture of different EPR's. Ideally, however a single copolymer is present.

In a preferred embodiment therefore, the resin consists essentially of components (A) and (B). The consists essentially of wording is used here to indicate the absence of other polyolefinic components. It will be appreciated that polymers contain additives and these may be present.

There should be more than 50 wt % of component (A) present in the heterophasic polypropylene resins of certain examples, such as 55 to 80 wt %, more preferably at least 60 wt % to 75 wt %.

Alternatively viewed, there should be more than 50 wt % of a xylene insoluble component present in the heterophasic polypropylene resins of certain examples, such as 55 to 80 wt %, more preferably at least 60 wt % to 75 wt % of a xylene insoluble component.

There should be at least 20 wt % of the EPR (B) fraction present but component (A) is in excess so there must be less than 50 wt % of component (B). Amounts of component (B) are preferably in the range of 21 to 49 wt %, such as 25 to 45 wt %, ideally 27 to 39 wt % of the heterophasic polypropylene resin.

The ethylene content of the EPR component (B) is preferably in the range of 21 to 49 wt %, such as 25 to 45 wt %.

Alternatively viewed, the xylene soluble (XS) fraction of the heterophasic resin of the invention is preferably 20 to less 50 wt %, such as 21 to 49 wt %, preferably 25 to 45 wt %, ideally 27 to 39 wt % of the heterophasic polypropylene resin.

The ethylene content of the XS fraction may be the range 20 to less than 50 wt %, such as 21 to 49 wt %, ideally 25 to 45 wt %.

It will be appreciated that the amount of XS fraction should essentially be the same as the amount of component (B) present as component (A) should contain almost no XS soluble components. Component (B) on the other hand should be almost completely xylene soluble.

The glass transition temperature of the XS fraction is preferably −30° C. or less, such as −35° C. or less.

In the following definitions, the term matrix component refers to the xylene insoluble component. This is essentially component (A) of the heterophasic propylene copolymer resin. The term XS fraction, XCS fraction or xylene soluble fraction refers to that component which is soluble in xylene. A definition of the XS test can be found in the test methods at the end of the description. Thus the XS fraction represents essentially the amorphous ethylene-propylene copolymer component and the insoluble fraction essentially represents the phase (A).

The intrinsic viscosity of the XS fraction is preferably in the range of 0.1 to 5 dl/g, preferably 0.2 to 1.75 dl/g, more preferably 0.5 to 1.7 dl/g, especially more preferably 0.75 to 1.7 dl/g determined according to DIN EN ISO 1628-1 and -3.

The $MFR_2$ of the XS fraction may be at least 10 g/10 min, such as at least 25 g/10 min. It might be in the range of 10 to 100 g/10 min.

The $MFR_2$ of the matrix component or xylene insoluble component is preferably less than 0.2 g/10 min, preferably less than 0.1 g/10 min, more preferably less than 0.05 g/10 min, especially less than 0.01 g/10 min.

If the MFR values for these components cannot be measured directly, they can be calculated from intrinsic viscosity measurements based on the correlations defined in C. Grein, M. Gahleitner, B. Knogler & S. Nestelberger, *Melt viscosity effects in Ethylene-Propylene Copolymers*, Rheol. Acta, 46 (2007) 1083-1089. From the MFR of the total polymer and the MFR of the XS fraction (sometimes called the XCS fraction), the MFR of the matrix component of an impact copolymer can be calculated using a logarithmic mixing rule, i.e. using the following equation $$MFR(Total) = 10^{(1-w(EPR))\log 10(MFR(Matrix)) + w(EPR)\log 10(MFR(XCS))}$$

with w(EPR) being the weight fraction of the elastomeric phase, approximated by the weight fraction of the XS component.

Thus the ratio of $MFR_2(XS)/MFR_2(matrix)$ is preferably at least 100, especially at least 350, more especially at least 500, such as at least 1000.

Alternatively viewed, the ratio of $MFR_2(XS)/MFR_2(xylene\ insoluble)$ is preferably at least 100, especially at least 350, more especially at least 500, such as at least 1000.

This represents therefore an enormous difference in molecular weight between the matrix component and the EPR component. The molecular weight of the EPR is significantly below that of the matrix. The matrix component therefore has a high Mw and the EPR component a low Mw.

The Mw of the XS fraction is preferably less than 150 kg/mol.

In contrast the Mw of the matrix component may exceed 1,000 kg/mol. Both components should possess narrow Mw/Mn values as they are produced using metallocene catalysis.

It is believed that this difference in Mw contributes to the remarkable impact properties which we observe. It is surprising that despite this significant molecular weight difference, the heterophasic polypropylene resins of this application are still homogeneous and we do not observe any incompatibility between the components.

The heterophasic polypropylene resin (as a whole) according to the invention preferably has a melt flow rate $MFR_2$ (2.16 kg, 230° C.) of 0.01 to 10 g/10 min, more preferably 0.01 to 5 g/10 min, most preferably 0.05 to 2 g/10 min.

The heterophasic polypropylene resin preferably shows excellent impact properties which can be seen as a high Charpy notched impact strength. The heterophasic polypropylene resin preferably has a Charpy notched impact strength at +23° C. of at least 90.0 kJim², such as at least 100 kJim². Our testing shows that at 23° C., the polymers of some examples remain unbroken, therefore exceeding the method limit of 150 kJim².

Further, the heterophasic polypropylene resin preferably has a Charpy notched impact strength at −20° C. of at least 25 kJ/m², preferably at least 50.0 kJ/m², more preferably at least 75.0 kJ/m², still more preferably at least 90.0 kJ/m².

Further, the polypropylene resin preferably has a brittle-to-ductile transition (BDTT) at a temperature of 0° C. or less, such as −10° C. or less, more preferably −15° C. or less, still more preferably of −20° C. or less, especially −25° C. or less determined from Charpy instrumented impact strength according to ISO 179-2:2000.

The polymers of various examples exhibit low stiffness in terms of low tensile modulus. Tensile modulus values of 50 to 800 MPa are therefore possible. This can provide flexibility to an article made using the heterophasic polypropylene resins of the invention.

The polymers of the invention are preferably manufactured using single site metallocene catalysts, especially asymmetrical metallocene catalysts. Thus in some examples, the complexes used to manufacture the polymers of the invention are asymmetrical. That means simply that the two indenylligands forming the metallocene are different, that is, each indenylligand bears a set of substituents that are either chemically different, or located in different positions with respect to the other indenylligand. More precisely, they are chiral, racemic bridged bisindenyl metallocenes.

Whilst the complexes may be in their syn configuration ideally, they are in their anti configuration. For the purpose of this invention, racemic-anti means that the two indenyl-ligands are oriented in opposite directions with respect to the cyclopentadienyl-metal-cyclopentadienyl plane, while racemic-syn means that the two indenylligands are oriented in the same direction with respect to the cyclopentadienyl-metal-cyclopentadienyl plane, as shown in the FIGURE below.

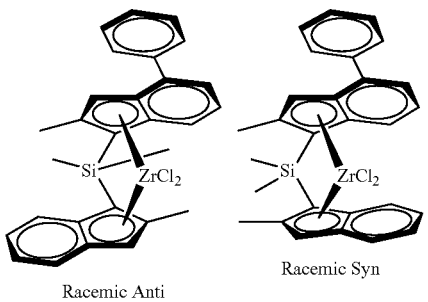

Racemic Anti    Racemic Syn

Formula (I) is intended to cover both syn and anti configurations, preferably anti. It is required in addition, that the group $R^{5'}$ is not hydrogen where the 5-position in the other ligand carries a hydrogen.

In fact, the metallocenes of use in certain examples are C1-symmetric but they maintain a pseudo-C2-symmetry since they maintain C2-symmetry in close proximity of the metal center, although not at the ligand periphery. As will be seen, the use of two different indenylligands as described in this invention allows for a much finer structural variation, hence a more precise tuning of the catalyst performance, compared to the typical C2-symmetric catalysts. By nature of their chemistry, both anti and syn enantiomer pairs are formed during the synthesis of the complexes. However, by using the ligands of this invention, separation of the preferred anti isomers from the syn isomers is straightforward.

It is preferred if the metallocenes of the invention are employed as the rac anti isomer. Ideally therefore at least 95% mol, such as at least 98% mol, especially at least 99% mol of the metallocene is in the racemic anti isomeric form.

In the catalysts of examples of the invention:

M is preferably Zr.

Each X, which may be the same or different, is preferably a hydrogen atom, a halogen atom, a R, OR, $OSO_2CF_3$, OCOR, SR, $NR_2$ or $PR_2$ group wherein R is a linear or branched, cyclic or acyclic, $C_{1-20}$ alkyl, $C_{2-20}$ alkenyl, $C_{2-20}$ alkynyl, $C_{6-20}$ aryl, $C_{7-20}$ alkylaryl or $C_{7-20}$ arylalkyl radical; optionally containing heteroatoms belonging to groups 14-16. R is preferably a $C_{1-6}$ alkyl, phenyl or benzyl group.

Most preferably each X is independently a hydrogen atom, a halogen atom, $C_{1-6}$ alkoxy group or an R group, e.g. preferably a $C_{1-6}$ alkyl, phenyl or benzyl group. Most preferably X is chlorine or a methyl radical. Preferably both X groups are the same.

L is preferably an alkylene linker or a bridge comprising a heteroatom, such as silicon or germanium, e.g. —$SiR^8_2$—, wherein each $R^8$ is independently $C_{1-20}$ alkyl, $C_{3-10}$ cycloakyl, $C_{6-20}$ aryl or tri($C_{1-20}$ alkyl)silyl, such as trimethylsilyl. More preferably $R^8$ is $C_{1-6}$ alkyl, especially methyl or $C_{3-7}$ cycloalkyl, such as cyclohexyl. Most preferably, L is a dimethylsilyl or a bridge (i.e. Me-Si-cyclohexyl). It may also be an ethylene bridge.

$R^2$ and $R^{2'}$ can be different but they are preferably the same. $R^2$ and $R^{2'}$ are preferably a $C_{1-10}$ hydrocarbyl group such as $C_{1-6}$ hydrocarbyl group. More preferably it is a linear or branched $C_{1-10}$ alkyl group. More preferably it is a linear or branched $C_{1-6}$ alkyl group, especially linear $C_{1-6}$ alkyl group such as methyl or ethyl.

The $R^2$ and $R^{2'}$ groups can be interrupted by one or more heteroatoms, such as 1 or 2 heteroatoms, e.g. one heteroatom, selected from groups 14 to 16 of the periodic table. Such a heteroatom is preferably O, N or S, especially O. More preferably however the $R^2$ and $R^{2'}$ groups are free from heteroatoms. Most preferably $R^2$ and $R^{2'}$ are methyl, especially both methyl.

The two Ar groups Ar and Ar' can be the same or different. It is preferred however if the Ar groups are different. The Ar' group may be unsubstituted. The Ar' is preferably a phenyl based group optionally substituted by groups $R^1$, especially an unsubstituted phenyl group.

The Ar group is preferably a $C_{6-20}$ aryl group such as a phenyl group or naphthyl group. Whilst the Ar group can be a heteroaryl group, such as carbazolyl, it is preferable that Ar is not a heteroaryl group. The Ar group can be unsubstituted or substituted by one or more groups $R^1$, more preferably by one or two $R^1$ groups, especially in position 4 of the aryl ring bound to the indenyl ligand or in the 3, 5-positions.

In one embodiment both Ar and Ar' are unsubstituted. In another embodiment Ar' is unsubstituted and Ar is substituted by one or two groups $R^1$.

$R^1$ is preferably a $C_{1-20}$ hydrocarbyl group, such as a $C_{1-20}$ alkyl group. $R^1$ groups can be the same or different, preferably the same. More preferably, $R^1$ is a $C_{2-10}$ alkyl group such as $C_{3-8}$ alkyl group. Highly preferred groups are tert butyl or isopropyl groups. It is preferred if the group $R^1$ is bulky, i.e. is branched. Branching might be alpha or beta to the ring. Branched $C_{3-8}$ alkyl groups are also favoured therefore.

In a further embodiment, two $R^1$ groups on adjacent carbon atoms taken together can form a fused 5 or 6 membered non aromatic ring with the Ar group, said ring being itself optionally substituted with one or more groups $R^4$. Such a ring might form a tetrahydroindenyl group with the Ar ring or a tetrahydronaphthyl group.

If an $R^4$ group is present, there is preferably only 1 such group. It is preferably a $C_{1-10}$ alkyl group.

It is preferred if there is one or two $R^1$ groups present on the Ar group. Where there is one $R^1$ group present, the group is preferably para to the indenyl ring (4-position). Where two $R^1$ groups are present these are preferably at the 3 and 5 positions.

$R^{5'}$ is preferably a $C_{1-20}$ hydrocarbyl group containing one or more heteroatoms from groups 14-16 and optionally substituted by one or more halo atoms or $R^{5'}$ is a $C_{1-10}$ alkyl group, such as methyl but most preferably it is a group $Z'R^{3'}$.

$R^6$ and $R^{6'}$ may be the same or different. In one preferred embodiment one of $R^6$ and $R^{6'}$ is hydrogen, especially $R^6$. It is preferred if $R^6$ and $R^{6'}$ are not both hydrogen. If not hydrogen, it is preferred if each $R^6$ and $R^{6'}$ is preferably a $C_{1-20}$ hydrocarbyl group, such as a $C_{1-20}$ alkyl group or $C_{6-10}$ aryl group. More preferably, $R^6$ and $R^{6'}$ are a $C_{2-10}$ alkyl group such as $C_{3-8}$ alkyl group. Highly preferred groups are tert-butyl groups. It is preferred if $R^6$ and $R^{6'}$ are bulky, i.e. are branched. Branching might be alpha or beta to the ring. Branched $C_{3-8}$ alkyl groups are also favoured therefore.

The $R^7$ and $R^{7'}$ groups can be the same or different. Each $R^7$ and $R^{7'}$ group is preferably hydrogen, a $C_{1-6}$ alkyl group or is a group $ZR^3$. It is preferred if $R^{7'}$ is hydrogen. It is preferred if $R^7$ is hydrogen, $C_{1-6}$ alkyl or $ZR^3$. The combination of both $R^7$ and $R^{7'}$ being hydrogen is most preferred.

It is also preferred if $ZR^3$ represents $OC_{1-6}$ alkyl, such as methoxy. It is also preferred is $R^7$ represents $C_{1-6}$ alkyl such as methyl.

Z and Z' are O or S, preferably O.

$R^3$ is preferably a $C_{1-10}$ hydrocarbyl group, especially a $C_{1-10}$ alkyl group, or aryl group optionally substituted by one or more halo groups. Most especially $R^3$ is a $C_{1-6}$ alkyl group, such as a linear $C_{1-6}$ alkyl group, e.g. methyl or ethyl $R^{3'}$ is preferably a $C_{1-10}$ hydrocarbyl group, especially a $C_{1-10}$ alkyl group, or aryl group optionally substituted by one or more halo groups. Most especially $R^{3'}$ is a $C_{1-6}$ alkyl group, such as a linear $C_{1-6}$ alkyl group, e.g. methyl or ethyl or it is a phenyl based radical optionally substituted with one or more halo groups such as Ph or $C_6F_5$.

Thus, preferred complexes of the invention are of formula (II') or (II)

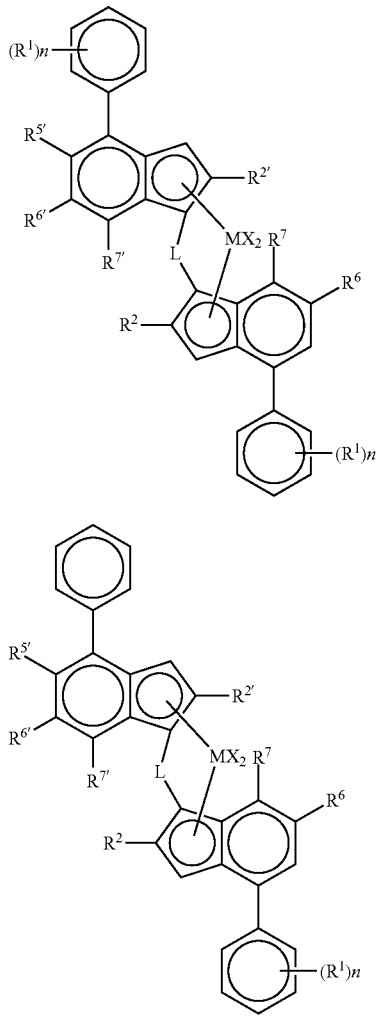

wherein

M is zirconium or hafnium;

each X is a sigma ligand, preferably each X is independently a hydrogen atom, a halogen atom, $C_{1-6}$ alkoxy group, $C_{1-6}$ alkyl, phenyl or benzyl group;

L is a divalent bridge selected from $-R'_2C-$, $-R'_2C-CR'_2-$, $-R'_2Si-$, $-R'_2Si-SiR'_2-$, $-R'_2Ge-$, wherein each R' is independently a hydrogen atom, $C_{1-20}$ alkyl, $C_{3-10}$ cycloalkyl, tri($C_{1-20}$-alkyl)silyl, $C_{6-20}$-aryl, $C_{7-20}$ arylalkyl or $C_{7-20}$ alkylaryl;

each $R^2$ or $R^{2'}$ is a $C_{1-10}$ alkyl group;

$R^{5'}$ is a $C_{1-10}$ alkyl group or $Z'R^{3'}$ group;

$R^6$ is hydrogen or a $C_{1-10}$ alkyl group;

$R^{6'}$ is a $C_{1-10}$ alkyl group or $C_{6-10}$ aryl group;

$R^7$ is hydrogen, a $C_{1-6}$ alkyl group or $ZR^3$ group;

$R^{7'}$ is hydrogen or a $C_{1-10}$ alkyl group;

Z and Z' are independently O or S;

$R^{3'}$ is a $C_{1-10}$ alkyl group, or a $C_{6-10}$ aryl group optionally substituted by one or more halo groups;

$R^3$ is a $C_{1-10}$-alkyl group;

Each n is independently 0 to 4, e.g. 0, 1 or 2;

and each $R^1$ is independently a $C_{1-20}$ hydrocarbyl group, e.g. $C_{1-10}$ alkyl group.

Further preferred complexes of the invention are those of formula (III) or (III'):

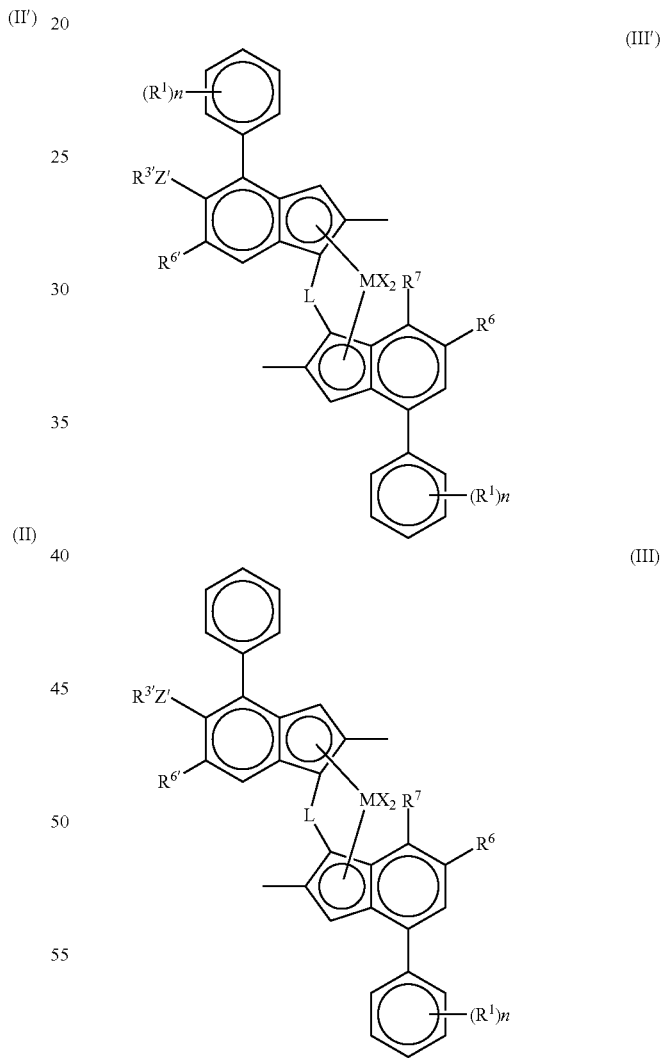

M is zirconium or hafnium;

each X is a sigma ligand, preferably each X is independently a hydrogen atom, a halogen atom, $C_{1-6}$ alkoxy group, $C_{1-6}$ alkyl, phenyl or benzyl group;

L is a divalent bridge selected from $-R'_2C-$ or $-R'_2Si-$ wherein each R' is independently a hydrogen atom, $C_{1-20}$ alkyl or $C_{3-10}$ cycloalkyl;

$R^6$ is hydrogen or a $C_{1-10}$ alkyl group;

$R^{6'}$ is a $C_{1-10}$ alkyl group or $C_{6-10}$ aryl group;

$R^7$ is hydrogen, $C_{1-6}$ alkyl or $OC_{1-6}$ alkyl;

Z' is O or S;

$R^{3'}$ is a $C_{1-10}$ alkyl group, or $C_{6-10}$ aryl group optionally substituted by one or more halo groups;

n is independently 0 to 4, e.g. 0, 1 or 2; and each $R^1$ is independently a $C_{1-10}$ alkyl group.

Further preferred complexes of use in the invention are those of formula (IV' or (IV):

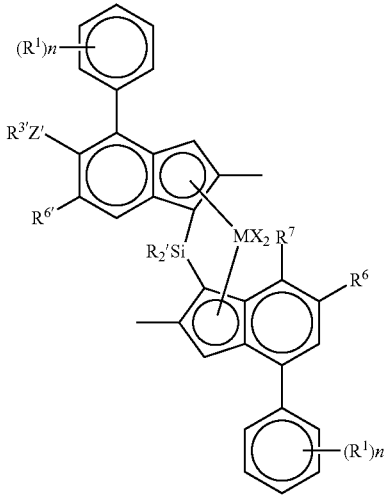

(IV')

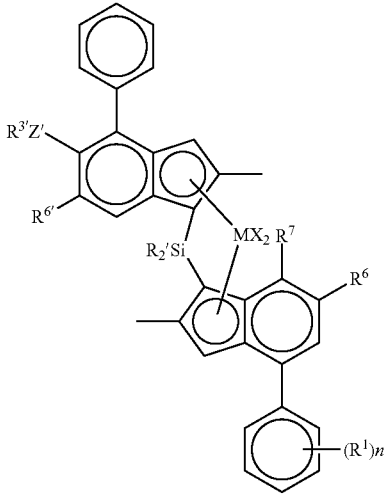

(IV)

M is zirconium or hafnium;

each X is a sigma ligand, preferably each X is independently a hydrogen atom, a halogen atom, $C_{1-6}$-alkoxy group, $C_{1-6}$-alkyl, phenyl or benzyl group;

each R' is independently a hydrogen atom, $C_{1-20}$ alkyl or $C_{3-7}$ cycloalkyl;

$R^6$ is hydrogen or a $C_{1-10}$ alkyl group;

$R^{6'}$ is a $C_{1-10}$ alkyl group or $C_{6-10}$ aryl group;

$R^7$ is hydrogen, $C_{1-6}$ alkyl or $OC_{1-6}$ alkyl;

Z' is O or S;

$R^{3'}$ is a $C_{1-10}$ alkyl group, or $C_{6-10}$ aryl group optionally substituted by one or more halo groups;

n is independently 0, 1 to 2; and each $R^1$ is independently a $C_{3-8}$ alkyl group.

Most especially, the preferred complex of use in the invention is of formula (V') or (V):

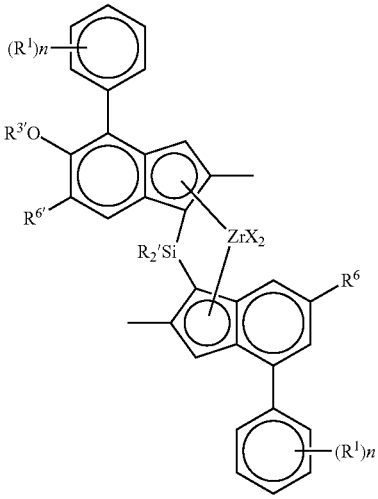

(V')

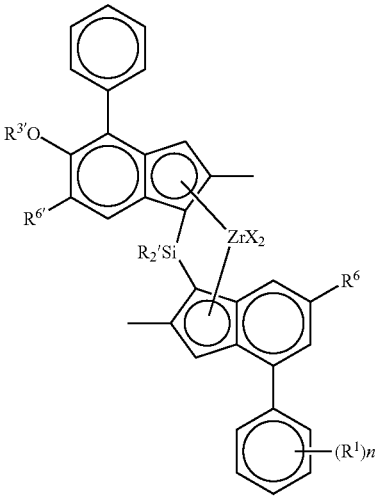

(V)

wherein each X is a sigma ligand, preferably each X is independently a hydrogen atom, a halogen atom, $C_{1-6}$-alkoxy group, $C_{1-6}$-alkyl, phenyl or benzyl group;

R' is independently a $C_{1-6}$ alkyl or $C_{3-10}$ cycloalkyl;

$R^1$ is independently $C_{3-8}$ alkyl;

$R^6$ is hydrogen or a $C_{3-8}$ alkyl group;

$R^{6'}$ is a $C_{3-8}$ alkyl group or $C_{6-10}$ aryl group;

$R^{3'}$ is a $C_{1-6}$ alkyl group, or $C_{6-10}$ aryl group optionally substituted by one or more halo groups; and n is independently 0, 1 or 2.

Particular compounds of the invention include:
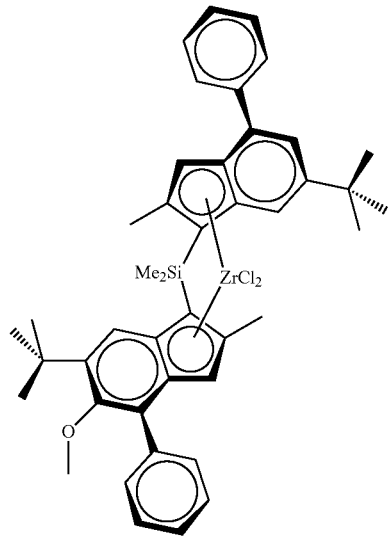
rac-anti-Me$_2$Si(2-Me-4-Ph-6-tBu-Ind)(2-Me-4-Ph-5-OMe-6-tBu-Ind)ZrCl$_2$
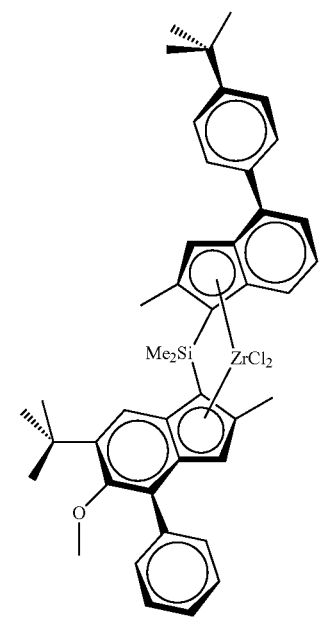
rac-anti-Me$_2$Si(2-Me-4-(p-tBuPh)-Ind)(2-Me-4-Ph-5-OMe-6-tBu-Ind)ZrCl$_2$
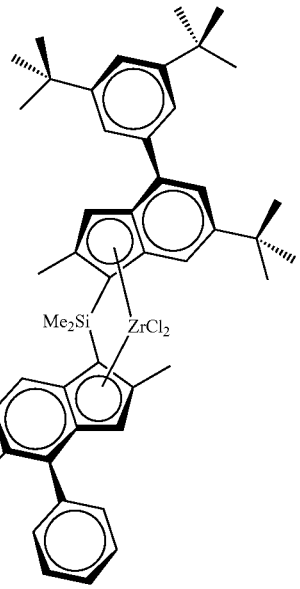
rac-anti-Me$_2$Si(2-Me-4-(3,5-di-tBuPh)-6-tBu-Ind)(2-Me-4-Ph-5-OMe-6-tBu-Ind)ZrCl$_2$
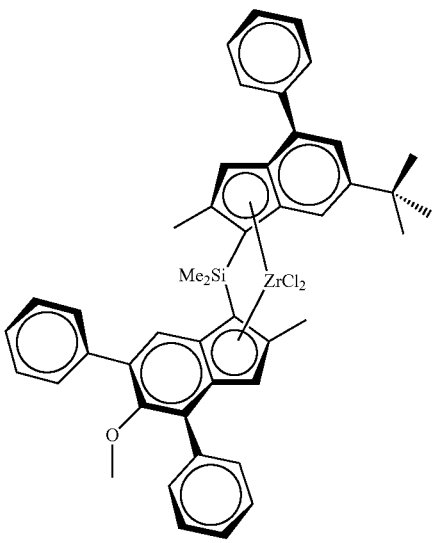
rac-anti-Me$_2$Si(2-Me-4-Ph-6-tBu-Ind)(2-Me-4,6-di-Ph-5-OMe-Ind)ZrCl$_2$

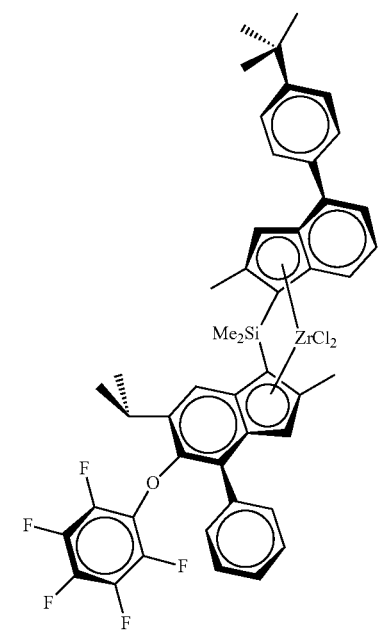
rac-anti-
Me₂Si(2-Me-
4-(p-tBuPh)-
Ind)(2-Me-4-
Ph-5-OC₆F₅)-
6-iPr-
Ind)ZrCl₂
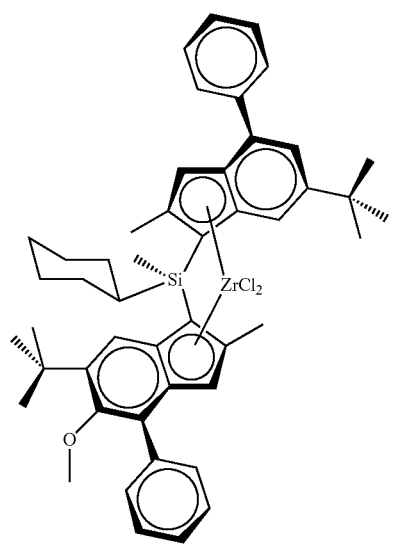
rac-anti-
Me(CyHex)Si(2-
Me-4-Ph-6-tBu-
Ind)(2-Me-4-Ph-
5-OMe-6-tBu-
Ind)ZrCl₂
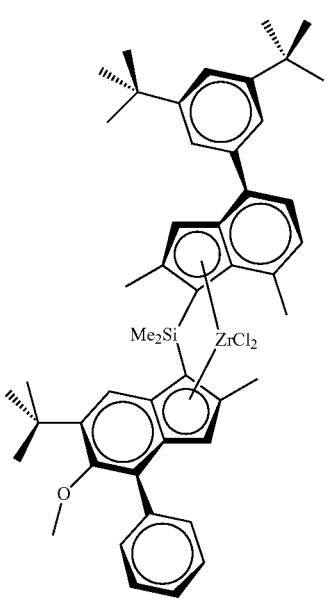
rac-anti-
Me₂Si(2-Me-
4-(3,5-di-
tBuPh)-7-Me-
Ind)(2-Me-4-
Ph-5-OMe-6-
tBu-Ind)ZrCl₂
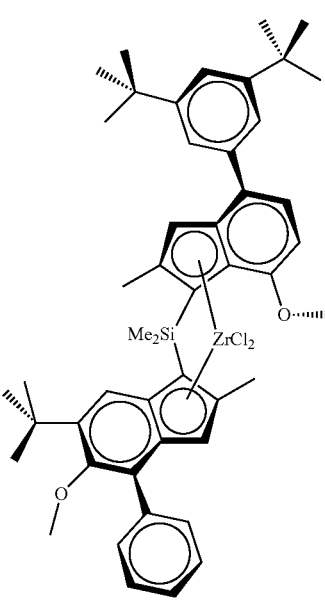
rac-anti-
Me₂Si(2-Me-4-
(3,5-di-tBuPh)-
7-OMe-Ind)(2-
Me-4-Ph-5-
OMe-6-tBu-
Ind)ZrCl₂

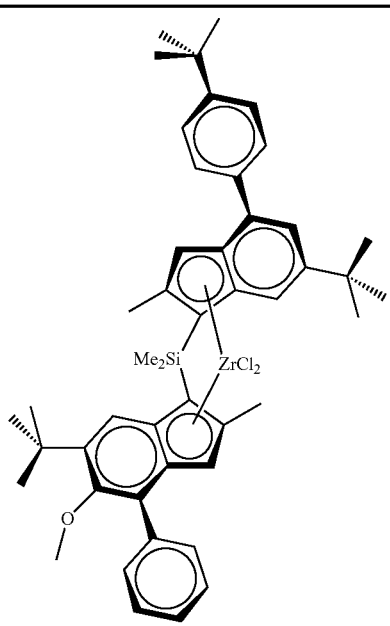

rac-anti-Me₂Si(2-
Me-4-(p-tBuPh)-6-
tBu-Ind)(2-Me-4-
Ph-5-OMe-6-tBu-
Ind)ZrCl₂

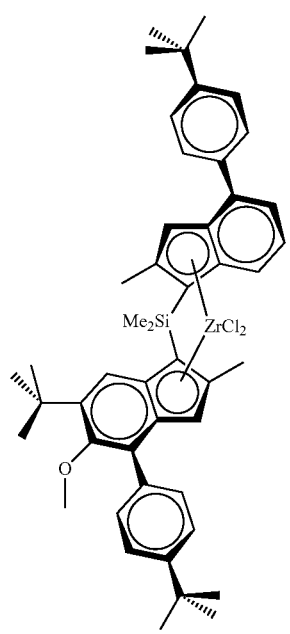

rac-anti-
Me₂Si(2-Me-4-
(p-tBuPh)-
Ind)(2-Me-4-(4-
tBuPh)-5-OMe-
6-tBu-Ind)ZrCl₂

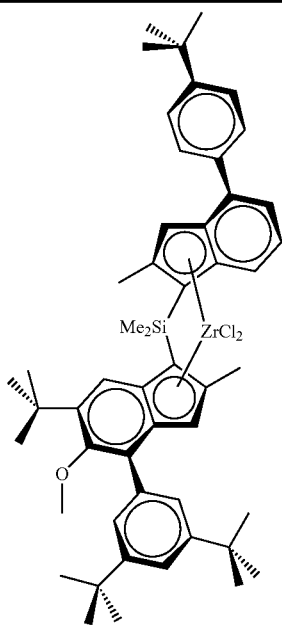

rac-anti-
Me₂Si(2-Me-4-
(p-tBuPh)-
Ind)(2-Me-4-
(3,5-tBu2Ph)-5-
OMe-6-tBu-
Ind)ZrCl₂

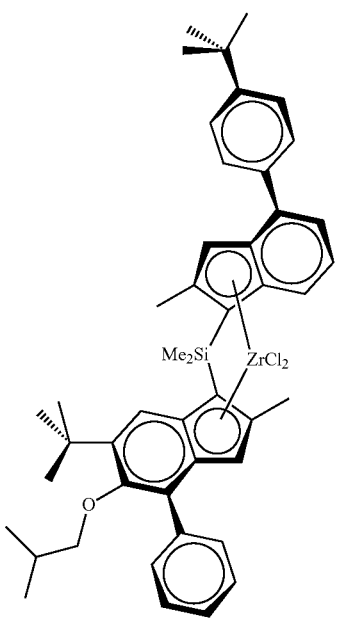

rac-anti-
Me₂Si(2-Me-
4-(p-tBuPh)-
Ind)(2-Me-4-
Ph-5-OiBu-6-
tBu-Ind)ZrCl₂

For the avoidance of doubt, any narrower definition of a substituent offered above can be combined with any other broad or narrowed definition of any other substituent.

Throughout the disclosure above, where a narrower definition of a substituent is presented, that narrower definition is deemed disclosed in conjunction with all broader and narrower definitions of other substituents in the application.

Synthesis

The ligands required to form the complexes and hence catalysts of use in the invention can be synthesised by any process and the skilled organic chemist would be able to devise various synthetic protocols for the manufacture of the necessary ligand materials.

For example, the following general synthetic scheme can be used:

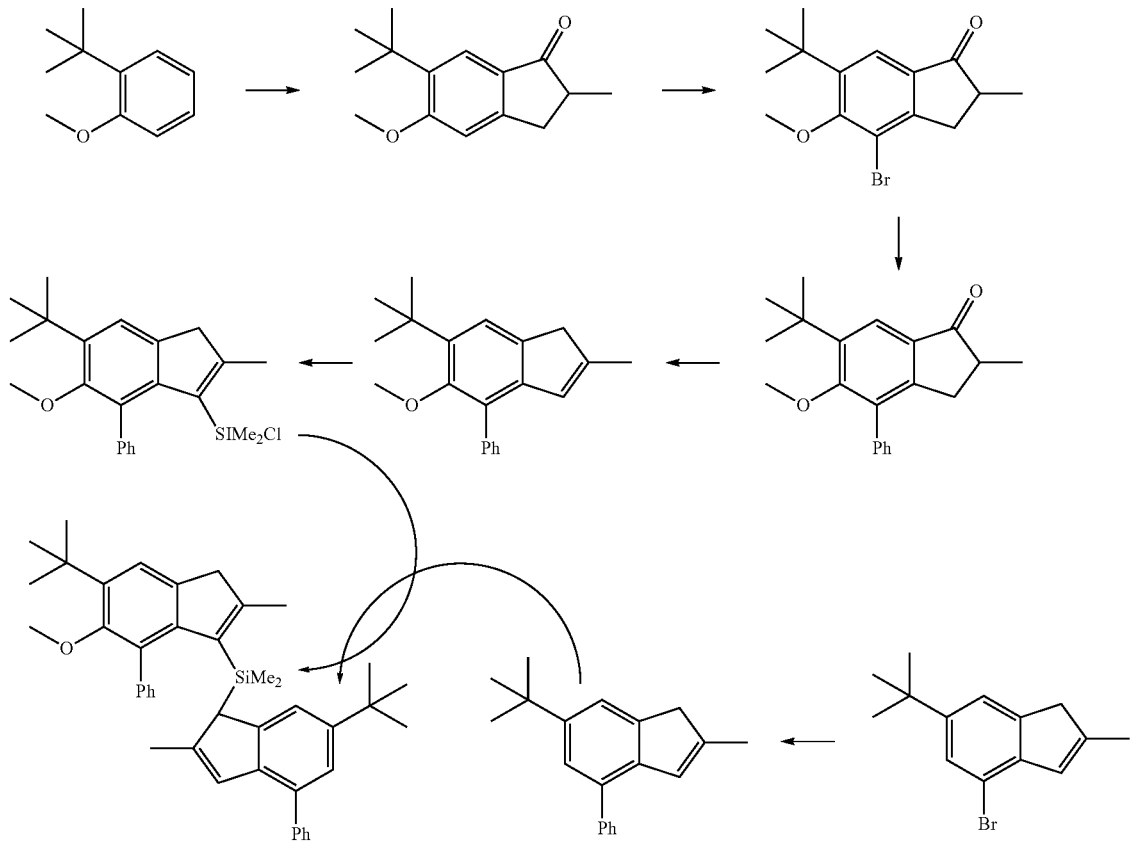

Scheme 1

Suitable reagents for this transformation are given in the examples section. Whilst this scheme refers to specific compounds, the general principles displayed here apply to the metallocenes of the invention. The important point to remember is that as the ligands are asymmetric, a conventional reaction with $SiMe_2Cl_2$ cannot be effected to bridge two ligands as that leads to symmetrical products. Instead, each ligand has to be attached to the bridge stepwise with control over the reaction stoichiometry.

Cocatalyst

To form an active catalytic species it is normally necessary to employ a cocatalyst as is well known in the art. Cocatalysts comprising one or more compounds of Group 13 metals, like organoaluminium compounds or borates used to activate metallocene catalysts are suitable for use in some examples.

The olefin polymerisation catalyst system may comprise (i) a complex in which the metal ion is coordinated by a ligand; and normally (ii) an aluminium alkyl compound (or other appropriate cocatalyst), or the reaction product thereof.

Thus the cocatalyst is preferably an alumoxane, like MAO or an alumoxane other than MAO.

Borate cocatalysts can also be employed. It will be appreciated by the skilled man that where boron based cocatalysts are employed, it is normal to preactivate the complex by reaction thereof with an aluminium alkyl compound, such as TIBA. This procedure is well known and any suitable aluminium alkyl, e.g. $Al(C_{1-6}\text{-alkyl})_3$. can be used.

Boron based cocatalysts of interest include those of formula $BY_3$ wherein Y is the same or different and is a hydrogen atom, an alkyl group of from 1 to about 20 carbon atoms, an aryl group of from 6 to about 15 carbon atoms, alkylaryl, arylalkyl, haloalkyl or haloaryl each having from 1 to 10 carbon atoms in the alkyl radical and from 6-20 carbon atoms in the aryl radical or fluorine, chlorine, bromine or iodine. Preferred examples for Y are methyl, propyl, isopropyl, isobutyl or trifluoromethyl, unsaturated groups such as aryl or haloaryl like phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl) phenyl. Preferred options are trifluoroborane, triphenylborane, tris(4-fluorophenyl)borane, tris(3,5-difluorophenyl)borane, tris(4-fluoromethylphenyl)borane, tris(2,4,6-trifluorophenyl)borane, tris(penta-fluorophenyl)borane, tris(tolyl)borane, tris(3,5-dimethyl-phenyl)borane, tris(3,5-difluorophenyl)borane and/or tris (3,4,5-trifluorophenyl)borane.

Particular preference is given to tris(pentafluorophenyl) borane.

It is preferred however is borates are used, i.e. compounds containing a borate 3+ ion. Such ionic cocatalysts preferably contain a non-coordinating anion such as tetrakis(pentafluorophenyl)borate and tetraphenylborate. Suitable counterions are protonated amine or aniline derivatives such as methylammonium, anilinium, dimethylammonium, diethylammonium, N-methylanilinium, diphenylammonium, N,N-dimethylanilinium, trimethylammonium, triethylammonium, tri-n-butylammonium, methyldiphenylammonium, pyridinium, p-bromo-N,N-dimethylanilinium or p-nitro-N,N-dimethylanilinium. Preferred ionic compounds which can be used according to the present invention include: triethylammoniumtetra(phenyl)borate, tributylammoniumtetra(phenyl)borate, trimethylammoniumtetra(tolyl)borate, tributylammoniumtetra(tolyl)borate, tributylammoniumtetra(pentafluorophenyl)borate, tripropylammoniumtetra(dimethylphenyl)borate, tributylammoniumtetra(trifluoromethylphenyl)borate, tributylammoniumtetra(4-fluorophenyl)borate, N,N-dimethylcyclohexylammoniumtetrakis(pentafluorophenyl) borate, N,N-dimethylbenzylammoniumtetrakis (pentafluorophenyl)borate, N,N-dimethylaniliniumtetra (phenyl)borate, N,N-diethylaniliniumtetra(phenyl)borate, N,N-dimethylaniliniumtetrakis(pentafluorophenyl)borate, N,N-di(propyl)ammoniumtetrakis(pentafluorophenyl)borate, di(cyclohexyl)ammoniumtetrakist(pentafluorophenyl) borate, triphenylphosphoniumtetrakis(phenyl)borate, triethylphosphoniumtetrakis(phenyl)borate, diphenylphosphoniumtetrakis(phenyl)borate, tri(methylphenyl)phosphoniumtetrakis(phenyl)borate, tri(dimethylphenyl)phosphoniumtetrakis(phenyl)borate, triphenylcarbeniumtetrakis(pentafluorophenyl)borate, or ferroceniumtetrakis (pentafluorophenyl)borate. Preference is given to triphenylcarbeniumtetrakis(pentafluorophenyl) borate, N,N-dimethylcyclohexylammoniumtetrakis(pentafluorophenyl) borate or N,N-dimethylbenzylammoniumtetrakis(pentafluorophenyl)borate.

The use of $B(C_6F_5)_3$, $C_6H_5N(CH_3)_2H:B(C_6F_5)_4$, $(C_6H_5)_3C:B(C_6F_5)_4$ or $Ni(CN)_4[B(C_6F_5)_3]_4^{2-}$ is especially preferred.

Suitable amounts of cocatalyst will be well known to the skilled man.

Catalyst Manufacture

The metallocene complex of the present invention can be used in combination with a suitable cocatalyst as a catalyst e.g. in a solvent such as toluene or an aliphatic hydrocarbon, (i.e. for polymerization in solution), as it is well known in the art. Preferably, polymerization takes place in the condensed phase or in gas phase.

The catalyst may be used in supported or unsupported form. The particulate support material used is preferably an organic or inorganic material, such as silica, alumina or zirconia or a mixed oxide such as silica-alumina, in particular silica, alumina or silica-alumina. The use of a silica support is preferred. The skilled man is aware of the procedures required to support a metallocene catalyst.

Especially preferably the support is a porous material so that the complex may be loaded into the pores of the support, e.g. using a process analogous to those described in WO94/14856 (Mobil), WO95/12622 (Borealis) and WO2006/097497. The particle size is not critical but is preferably in the range 5 to 200 µm, more preferably 20 to 80 µm. The use of these supports is routine in the art.

In an alternative embodiment, no support is used at all. Such a catalyst can be prepared in solution, for example in an aromatic solvent like toluene, by contacting the metallocene (as a solid or as a solution) with the cocatalyst, for example methylaluminoxane or a borane or a borate salt previously dissolved in an aromatic solvent, or can be prepared by sequentially adding the dissolved catalyst components to the polymerization medium. In a preferred embodiment, the metallocene (when X differs from alkyl or hydrogen) is prereacted with an aluminum alkyl, in a ratio metal/aluminum of from 1:1 up to 1:500, preferably from 1:1 up to 1:250, and then combined with a solution of the borane or borate cocatalyst dissolved in an aromatic solvent, either in a separate vessel or directly into the polymerization reactor. Preferred metal/boron ratios are between 1:1 and 1:100, more preferably 1:1 to 1:10.

In one particularly preferred embodiment, no external carrier is used but the catalyst is still presented in solid particulate form. Thus no external support material such as inert organic or inorganic carrier, such as for example silica as described above is employed.

In order to provide the catalyst of the invention in solid form but without using an external carrier, it is preferred if a liquid/liquid emulsion system is used. The process involves forming dispersing catalyst components (i) and (ii) in a solvent, and solidifying said dispersed droplets to form solid particles.

In particular, the method involves preparing a solution of one or more catalyst components; dispersing said solution in an solvent to form an emulsion in which said one or more catalyst components are present in the droplets of the dispersed phase; immobilising the catalyst components in the dispersed droplets, in the absence of an external particulate porous support, to form solid particles comprising the said catalyst, and optionally recovering said particles.

This process enables the manufacture of active catalyst particles with improved morphology, e.g. with a predetermined spherical shape, surface properties and particle size and without using any added external porous support material, such as an inorganic oxide, e.g. silica. By the term "preparing a solution of one or more catalyst components" is meant that the catalyst forming compounds may be combined in one solution which is dispersed to the immiscible solvent, or, alternatively, at least two separate catalyst solutions for each part of the catalyst forming compounds may be prepared, which are then dispersed successively to the solvent.

In a preferred method for forming the catalyst at least two separate solutions for each or part of said catalyst may be prepared, which are then dispersed successively to the immiscible solvent.

More preferably, a solution of the complex comprising the transition metal compound and the cocatalyst is combined with the solvent to form an emulsion wherein that inert solvent forms the continuous liquid phase and the solution comprising the catalyst components forms the dispersed phase (discontinuous phase) in the form of dispersed droplets. The droplets are then solidified to form solid catalyst particles, and the solid particles are separated from the liquid and optionally washed and/or dried. The solvent forming the continuous phase may be immiscible to the catalyst solution at least at the conditions (e.g. temperatures) used during the dispersing step.

The term "immiscible with the catalyst solution" means that the solvent (continuous phase) is fully immiscible or partly immiscible i.e. not fully miscible with the dispersed phase solution.

Preferably said solvent is inert in relation to the compounds of the catalyst system to be produced. Full disclosure of the necessary process can be found in WO03/051934 which is herein incorporated by reference.

The inert solvent must be chemically inert at least at the conditions (e.g. temperature) used during the dispersing step. Preferably, the solvent of said continuous phase does not contain dissolved therein any significant amounts of catalyst forming compounds. Thus, the solid particles of the catalyst are formed in the droplets from the compounds which originate from the dispersed phase (i.e. are provided to the emulsion in a solution dispersed into the continuous phase).

The terms "immobilisation" and "solidification" are used herein interchangeably for the same purpose, i.e. for forming free flowing solid catalyst particles in the absence of an external porous particulate carrier, such as silica. The solidification happens thus within the droplets. Said step can be effected in various ways as disclosed in said WO03/051934 Preferably solidification is caused by an external stimulus to the emulsion system such as a temperature change to cause the solidification. Thus in said step the catalyst component (s) remain "fixed" within the formed solid particles. It is also possible that one or more of the catalyst components may take part in the solidification/immobilisation reaction.

Accordingly, solid, compositionally uniform particles having a predetermined particle size range can be obtained.

Furthermore, the particle size of the catalyst particles of the invention can be controlled by the size of the droplets in the solution, and spherical particles with a uniform particle size distribution can be obtained.

The invention is also industrially advantageous, since it enables the preparation of the solid particles to be carried out as a one-pot procedure. Continuous or semicontinuous processes are also possible for producing the catalyst.

Dispersed Phase

The principles for preparing two phase emulsion systems are known in the chemical field. Thus, in order to form the two phase liquid system, the solution of the catalyst component (s) and the solvent used as the continuous liquid phase have to be essentially immiscible at least during the dispersing step. This can be achieved in a known manner e.g. by choosing said two liquids and/or the temperature of the dispersing step/solidifying step accordingly.

A solvent may be employed to form the solution of the catalyst component (s). Said solvent is chosen so that it dissolves said catalyst component (s). The solvent can be preferably an organic solvent such as used in the field, comprising an optionally substituted hydrocarbon such as linear or branched aliphatic, alicyclic or aromatic hydrocarbon, such as a linear or cyclic alkane, an aromatic hydrocarbon and/or a halogen containing hydrocarbon.

Examples of aromatic hydrocarbons are toluene, benzene, ethylbenzene, propylbenzene, butylbenzene and xylene. Toluene is a preferred solvent. The solution may comprise one or more solvents. Such a solvent can thus be used to facilitate the emulsion formation, and usually does not form part of the solidified particles, but e.g. is removed after the solidification step together with the continuous phase.

Alternatively, a solvent may take part in the solidification, e.g. an inert hydrocarbon having a high melting point (waxes), such as above 40° C., suitably above 70° C., e.g. above 80° C. or 90° C., may be used as solvents of the dispersed phase to immobilise the catalyst compounds within the formed droplets.

In another embodiment, the solvent consists partly or completely of a liquid monomer, e.g. liquid olefin monomer designed to be polymerised in a "prepolymerisation" immobilisation step.

Continuous Phase

The solvent used to form the continuous liquid phase is a single solvent or a mixture of different solvents and may be immiscible with the solution of the catalyst components at least at the conditions (e.g. temperatures) used during the dispersing step. Preferably said solvent is inert in relation to said compounds.

The term "inert in relation to said compounds" means herein that the solvent of the continuous phase is chemically inert, i.e. undergoes no chemical reaction with any catalyst forming component. Thus, the solid particles of the catalyst are formed in the droplets from the compounds which originate from the dispersed phase, i.e. are provided to the emulsion in a solution dispersed into the continuous phase.

It is preferred that the catalyst components used for forming the solid catalyst will not be soluble in the solvent of the continuous liquid phase. Preferably, said catalyst components are essentially insoluble in said continuous phase forming solvent.

Solidification takes place essentially after the droplets are formed, i.e. the solidification is effected within the droplets e.g. by causing a solidifying reaction among the compounds present in the droplets. Furthermore, even if some solidifying agent is added to the system separately, it reacts within the droplet phase and no catalyst forming components go into the continuous phase.

The term "emulsion" used herein covers both bi- and multiphasic systems.

In a preferred embodiment said solvent forming the continuous phase is an inert solvent including a halogenated organic solvent or mixtures thereof, preferably fluorinated organic solvents and particularly semi, highly or perfluorinated organic solvents and functionalised derivatives thereof. Examples of the above-mentioned solvents are semi, highly or perfluorinated hydrocarbons, such as alkanes, alkenes and cycloalkanes, ethers, e.g. perfluorinated ethers and amines, particularly tertiary amines, and functionalised derivatives thereof. Preferred are semi, highly or perfluorinated, particularly perfluorinated hydrocarbons, e.g. perfluorohydrocarbons of e.g. C3-C30, such as C4-C10. Specific examples of suitable perfluoroalkanes and perfluorocycloalkanes include perfluoro-hexane, -heptane, -octane and -(methylcyclohexane). Semi fluorinated hydrocarbons relates particularly to semifluorinated n-alkanes, such as perfluoroalkyl-alkane.

"Semi fluorinated" hydrocarbons also include such hydrocarbons wherein blocks of —C—F and —C—H alternate. "Highly fluorinated" means that the majority of the —C—H units are replaced with —C—F units. "Perfluorinated" means that all —C—H units are replaced with —C—F units. See the articles of A. Enders and G. Maas in "Chemie in unserer Zeit", 34. Jahrg. 2000, Nr.6, and of Pierandrea Lo Nostro in "Advances in Colloid and Interface Science", 56 (1995) 245-287, Elsevier Science.

Dispersing Step

The emulsion can be formed by any means known in the art: by mixing, such as by stirring said solution vigorously to said solvent forming the continuous phase or by means of mixing mills, or by means of ultra sonic wave, or by using a so called phase change method for preparing the emulsion by first forming a homogeneous system which is then transferred by changing the temperature of the system to a biphasic system so that droplets will be formed.

The two phase state is maintained during the emulsion formation step and the solidification step, as, for example, by appropriate stirring.

Additionally, emulsifying agents/emulsion stabilisers can be used, preferably in a manner known in the art, for facilitating the formation and/or stability of the emulsion. For the said purposes e.g. surfactants, e.g. a class based on hydrocarbons (including polymeric hydrocarbons with a molecular weight e.g. up to 10 000 and optionally interrupted with a heteroatom(s)), preferably halogenated hydrocarbons, such as semi- or highly fluorinated hydrocarbons optionally having a functional group selected e.g. from —OH, —SH, $NH_2$, $NR''_2$.—COOH, —$COONH_2$, oxides of alkenes, —CR''=$CH_2$, where R'' is hydrogen, or C1-C20 alkyl, C2-20-alkenyl or C2-20-alkynyl group, oxo-groups, cyclic ethers and/or any reactive derivative of these groups, like alkoxy, or carboxylic acid alkyl ester groups, or, preferably semi-, highly- or perfluorinated hydrocarbons having a functionalised terminal, can be used. The surfactants can be added to the catalyst solution, which forms the dispersed phase of the emulsion, to facilitate the forming of the emulsion and to stabilize the emulsion.

Alternatively, an emulsifying and/or emulsion stabilising aid can also be formed by reacting a surfactant precursor bearing at least one functional group with a compound reactive with said functional group and present in the catalyst solution or in the solvent forming the continuous phase. The obtained reaction product acts as the actual emulsifying aid and or stabiliser in the formed emulsion system.

Examples of the surfactant precursors usable for forming said reaction product include e.g. known surfactants which bear at least one functional group selected e.g. from —OH, —SH, $NH_2$, $NR''_2$.— COOH, —$COONH_2$, oxides of alkenes, —CR''=$CH_2$, where R'' is hydrogen, or C1-C20 alkyl, C2-20-alkenyl or C2-20-alkynyl group, oxo-groups, cyclic ethers with 3 to 5 ring atoms, and/or any reactive derivative of these groups, like alkoxy or carboxylic acid alkyl ester groups; e.g. semi-, highly or perfluorinated hydrocarbons bearing one or more of said functional groups. Preferably, the surfactant precursor has a terminal functionality as defined above.

The compound reacting with such surfactant precursor is preferably contained in the catalyst solution and may be a further additive or one or more of the catalyst forming compounds. Such compound is e.g. a compound of group 13 (e.g. MAO and/or an aluminium alkyl compound and/or a transition metal compound).

If a surfactant precursor is used, it is preferably first reacted with a compound of the catalyst solution before the addition of the transition metal compound. In one embodiment e.g. a highly fluorinated C1-n (suitably C4-30- or C5-15) alcohol (e.g. highly fluorinated heptanol, octanol or nonanol), oxide (e.g. propenoxide) or acrylate ester is reacted with a cocatalyst to form the "actual" surfactant. Then, an additional amount of cocatalyst and the transition metal compound is added to said solution and the obtained solution is dispersed to the solvent forming the continuous phase. The "actual" surfactant solution may be prepared before the dispersing step or in the dispersed system. If said solution is made before the dispersing step, then the prepared "actual" surfactant solution and the transition metal solution may be dispersed successively (e.g. the surfactant solution first) to the immiscible solvent, or be combined together before the dispersing step.

Solidification

The solidification of the catalyst component(s) in the dispersed droplets can be effected in various ways, e.g. by causing or accelerating the formation of said solid catalyst forming reaction products of the compounds present in the droplets. This can be effected, depending on the used compounds and/or the desired solidification rate, with or without an external stimulus, such as a temperature change of the system.

In a particularly preferred embodiment, the solidification is effected after the emulsion system is formed by subjecting the system to an external stimulus, such as a temperature change. Temperature differences of e.g. 5 to 100° C., such as 10 to 100° C., or 20 to 90° C., such as 50 to 90° C.

The emulsion system may be subjected to a rapid temperature change to cause a fast solidification in the dispersed system. The dispersed phase may e.g. be subjected to an immediate (within milliseconds to few seconds) temperature change in order to achieve an instant solidification of the component (s) within the droplets. The appropriate temperature change, i.e. an increase or a decrease in the temperature of an emulsion system, required for the desired solidification rate of the components cannot be limited to any specific range, but naturally depends on the emulsion system, i. a. on the used compounds and the concentrations/ratios thereof, as well as on the used solvents, and is chosen accordingly. It is also evident that any techniques may be used to provide sufficient heating or cooling effect to the dispersed system to cause the desired solidification.

In one embodiment the heating or cooling effect is obtained by bringing the emulsion system with a certain temperature to an inert receiving medium with significantly different temperature, e.g. as stated above, whereby said temperature change of the emulsion system is sufficient to cause the rapid solidification of the droplets. The receiving medium can be gaseous, e.g. air, or a liquid, preferably a solvent, or a mixture of two or more solvents, wherein the catalyst component (s) is (are) immiscible and which is inert in relation to the catalyst component (s). For instance, the receiving medium comprises the same immiscible solvent used as the continuous phase in the first emulsion formation step.

Said solvents can be used alone or as a mixture with other solvents, such as aliphatic or aromatic hydrocarbons, such as alkanes. Preferably a fluorinated solvent as the receiving medium is used, which may be the same as the continuous phase in the emulsion formation, e.g. perfluorinated hydrocarbon.

Alternatively, the temperature difference may be effected by gradual heating of the emulsion system, e.g. up to 10° C. per minute, preferably 0.5 to 6° C. per minute and more preferably in 1 to 5° C. per minute.

In case a melt of e.g. a hydrocarbon solvent is used for forming the dispersed phase, the solidification of the droplets may be effected by cooling the system using the temperature difference stated above.

Preferably, the "one phase" change as usable for forming an emulsion can also be utilised for solidifying the catalytically active contents within the droplets of an emulsion system by, again, effecting a temperature change in the dispersed system, whereby the solvent used in the droplets becomes miscible with the continuous phase, preferably a fluorous continuous phase as defined above, so that the droplets become impoverished of the solvent and the solidifying components remaining in the "droplets" start to solidify. Thus the immiscibility can be adjusted with respect to the solvents and conditions (temperature) to control the solidification step.

The miscibility of e.g. organic solvents with fluorous solvents can be found from the literature and be chosen accordingly by a skilled person. Also the critical temperatures needed for the phase change are available from the literature or can be determined using methods known in the art, e.g. the Hildebrand-Scatchard-Theorie. Reference is also made to the articles of A. Enders and G. and of Pierandrea Lo Nostro cited above.

Thus according to the invention, the entire or only part of the droplet may be converted to a solid form. The size of the "solidified" droplet may be smaller or greater than that of the original droplet, e.g. if the amount of the monomer used for the prepolymerisation is relatively large.

The solid catalyst particles recovered can be used, after an optional washing step, in a polymerisation process of an olefin. Alternatively, the separated and optionally washed solid particles can be dried to remove any solvent present in the particles before use in the polymerisation step. The separation and optional washing steps can be effected in a known manner, e.g. by filtration and subsequent washing of the solids with a suitable solvent.

The droplet shape of the particles may be substantially maintained. The formed particles may have an average size range of 1 to 500 μm, e.g. 5 to 500 μm, advantageously 5 to 200 μm or 10 to 150 μm. Even an average size range of 5 to 60 μm is possible. The size may be chosen depending on the polymerisation the catalyst is used for. Advantageously, the particles are essentially spherical in shape, they have a low porosity and a low surface area.

The formation of solution can be effected at a temperature of 0-100° C., e.g. at 20-80° C. The dispersion step may be effected at −20° C.-100° C., e.g. at about −10-70° C., such as at −5 to 30° C., e.g. around 0° C.

To the obtained dispersion an emulsifying agent as defined above, may be added to improve/stabilise the droplet formation. The solidification of the catalyst component in the droplets is preferably effected by raising the temperature of the mixture, e.g. from 0° C. temperature up to 100° C., e.g. up to 60-90° C., gradually. E.g. in 1 to 180 minutes, e.g. 1-90 or 5-30 minutes, or as a rapid heat change. Heating time is dependent on the size of the reactor.

During the solidification step, which is preferably carried out at about 60 to 100° C., preferably at about 75 to 95° C., (below the boiling point of the solvents) the solvents may preferably be removed and optionally the solids are washed with a wash solution, which can be any solvent or mixture of solvents such as those defined above and/or used in the art, preferably a hydrocarbon, such as pentane, hexane or heptane, suitably heptane. The washed catalyst can be dried or it can be slurried into an oil and used as a catalyst-oil slurry in polymerisation process.

All or part of the preparation steps can be done in a continuous manner. Reference is made to WO2006/069733 describing principles of such a continuous or semicontinuous preparation methods of the solid catalyst types, prepared via emulsion/solidification method.

Polymerisation

The polymers of the invention can be prepared by blending the necessary components that have been formed separately. However, the polymers are typically (and preferably) made in a multistep process well known in the art. A preferred multistage process is a "loop-gas phase"-process, such as developed by Borealis A/S, Denmark (known as BORSTAR® technology) described e.g. in patent literature, such as in EP 0 887 379 or in WO 92/12182.

Polymerization in the method of the invention may be effected in one or more, e.g. 1 or 2, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase reactors. The heterophasic polypropylene resin according to this invention is ideally produced in a multistage process in a multi-stage reaction sequence. Thereby it is preferred that the propylene homopolymer matrix (A) is produced in the bulk reactor and afterwards transferred to the gas phase reactor in which the ethylene-propylene rubber phase (B) is produced in the presence of component (A). The bulk polymerisations are preferably performed in a so-called loop reactor.

In case of propylene polymerisation for loop reactors, the reaction temperature will generally be in the range 60 to 110° C. (e.g. 60-90° C.), the reactor pressure will generally be in the range 5 to 80 bar (e.g. 20-60 bar), and the residence time will generally be in the range 0.1 to 5 hours (e.g. 0.3 to 2 hours). The monomer is usually used as reaction medium.

For gas phase reactors, the reaction temperature used will generally be in the range 60 to 115° C. (e.g. 70 to 110° C.), the reactor pressure will generally be in the range 10 to 25 bar, and the residence time will generally be 0.5 to 8 hours (e.g. 0.5 to 4 hours). The gas used will be the monomer optionally as mixture with a non-reactive gas such as nitrogen or propane. In addition to actual polymerisation steps and reactors, the process can contain any additional polymerisation steps, like prepolymerisation step, and any further after reactor handling steps as known in the art.

For solution polymerization, an aliphatic or aromatic solvent can be used to dissolve the monomer and the polymer, and the polymerization temperature will generally be in the range 80 to 200° C. (e.g. 90 to 150° C.).

The process of the invention may also comprise a prepolymerisation step in a manner known in the field and which may precede the first polymerisation step.

The residence time can vary in both reactor zones. In one embodiment of the process for producing the propylene polymer the residence time in bulk reactor, e.g. loop is in the range 0.5 to 5 hours, e.g. 0.5 to 2 hours and the residence time in gas phase reactor will generally be 1 to 8 hours.

If desired, the polymerisation may be effected in a known manner under supercritical conditions in the bulk, preferably loop reactor, and/or as a condensed mode in the gas phase reactor.

Generally the quantity of catalyst used will depend upon the nature of the catalyst, the reactor types and conditions and the properties desired for the polymer product. As is well known in the art hydrogen can be used for controlling the molecular weight of the polymer.

Polymers obtained with the metallocenes of certain examples have normal particle morphologies.

Heterophasic copolymers can be prepared with example catalysts and the activity of this catalyst in both liquid and gas phase is much better than that obtained with a standard symmetrical metallocene. The higher activity in bulk and gas phase makes those examples the preferred catalyst over symmetrical ones.

In general therefore example catalysts can provide:

high activity in bulk propylene polymerisation;

very high molecular weight capability (Mw>900 kg/mol);

improved ethylene incorporation in propylene copolymers;

high activity obtained in C2/C3 copolymerization in gas phase;

good polymer morphology.

It is a feature of certain examples that the claimed catalysts enable the formation of polymers with high molecular weight. These features can be achieved at commercially interesting polymerisation temperatures, e.g. 60° C. or more. It is a preferred feature of some examples that the catalysts are used to polymerise propylene at a temperature of at least 60° C., preferably at least 65° C., such as at least 70° C.

The heterophasic polypropylene resin of the invention can be used in the manufacture of an article such as a flexible pipe/tube, profile, cable insulation, sheet or film. These articles are useful in the medical and general packaging area but also for technical purposes like electrical power cables or geomembranes. Alternatively, the heterophasic polypropylene resin can be used in impact modification of a composition for injection moulding of articles, such as for technical applications in the automotive area.

For impact modification, between 5 and 50 wt % of the inventive heterophasic polypropylene resin will be added to another polypropylene resin having a significantly higher MFR than the inventive heterophasic polypropylene resin.

Thus, the invention also relates to polymer blends comprising the heterophasic polypropylene resins of the invention, in particular blends of it with other propylene polymers. The heterophasic polypropylene copolymer of the invention may form 5 to 50 wt % of such a blend, such as 10 to 40 wt %, in particular 15 to 30 wt % of such a blend.

The heterophasic polypropylene copolymer might be mixed with a polypropylene having a higher $MFR_2$, such as at least 10 g/10 min. In particular, it can be mixed with polypropylenes used in car parts. Such polypropylenes may be homopolymers. Preferably they will not be other elastomeric polymers like another EPR.

The polymers of certain examples are useful in the manufacture of a variety of end articles such as films (cast, blown or BOPP films), moulded articles (e.g. injection moulded, blow moulded, rotomoulded articles), extrusion coatings and so on. Preferably, articles comprising the films of some examples of are used in packaging. Packaging of interest include heavy duty sacks, hygiene films, lamination films, and soft packaging films.

Due to their excellent low temperature properties, films of certain examples are ideal for use in frozen packaging.

The invention will now be illustrated by reference to the following non-limiting examples and figures. The scope of the invention includes heterophasic polypropylene resins as hereinbefore defined, e.g. in the claims, except those recited in examples 1 to 3 below. The scope of the invention includes heterophasic polypropylene resins as hereinbefore defined, e.g. in the claims, including those recited in examples 1 to 3 below. The invention also provides the examples below as specific embodiments of the invention.

FIG. 1 shows brittle-to-ductile transition curves for SSC-based inventive and comparative examples.

ANALYTICAL TESTS

Measurement Methods:
Al and Zr Determination (ICP-Method)

The elementary analysis of a catalyst was performed by taking a solid sample of mass, M, cooling over dry ice. Samples were diluted up to a known volume, V, by dissolving in nitric acid ($HNO_3$, 65%, 5% of V) and freshly deionised (DI) water (5% of V). The solution was then added to hydrofluoric acid (HF, 40%, 3% of V), diluted with DI water up to the final volume, V, and left to stabilise for two hours.

The analysis was run at room temperature using a Thermo Elemental iCAP 6300 Inductively Coupled Plasma-Optical Emmision Spectrometer (ICP-OES) which was calibrated using a blank (a solution of 5% $HNO_3$, 3% HF in DI water), and 6 standards of 0.5 ppm, 1 ppm, 10 ppm, 50 ppm, 100 ppm and 300 ppm of Al, with 0.5 ppm, 1 ppm, 5 ppm, 20 ppm, 50 ppm and 100 ppm of Hf and Zr in solutions of 5% HNO3, 3% HF in DI water.

Immediately before analysis the calibration is 'resloped' using the blank and 100 ppm Al, 50 ppm Hf, Zr standard, a quality control sample (20 ppm Al, 5 ppm Hf, Zr in a solution of 5% HNO3, 3% HF in DI water) is run to confirm the reslope. The QC sample is also run after every 5th sample and at the end of a scheduled analysis set.

The content of hafnium was monitored using the 282.022 nm and 339.980 nm lines and the content for zirconium using 339.198 nm line. The content of aluminium was monitored via the 167.079 nm line, when Al concentration in ICP sample was between 0-10 ppm (calibrated only to 100 ppm) and via the 396.152 nm line for Al concentrations above 10 ppm.

The reported values are an average of three successive aliquots taken from the same sample and are related back to the original catalyst by inputting the original mass of sample and the dilution volume into the software.

DSC Analysis

The melting point ($T_m$) and crystallization temperature ($T_c$) were determined on a DSC200 TA instrument, by placing a 5-7 mg polymer sample, into a closed DSC aluminum pan, heating the sample from −10° C. to 210° C. at 10° C./min, holding for 5 min at 210° C., cooling from 210° C. to −10° C., holding for 5 min at −10° C., heating from −10° C. to 210° C. at 10° C./min. The reported $T_m$ is the maximum of the curve from the second heating scan and $T_c$ is the maximum of the curve of the cooling scan.

Melt Flow Rate

The melt flow rate (MFR) is determined according to ISO 1133 and is indicated in g/10 min. The MFR is an indication of the flowability, and hence the processability, of the polymer. The higher the melt flow rate, the lower the viscosity of the polymer. The MFR is determined at 230° C. and may be determined at different loadings such as 2.16 kg ($MFR_2$) or 21.6 kg ($MFR_{21}$).

The MFR of the XS fraction can also be calculated from the intrinsic viscosity (IV) of said fraction using the correlations defined in C. Grein, M. Gahleitner, B. Knogler & S. Nestelberger, Melt viscosity effects in Ethylene-Propylene Copolymers, Rheol. Acta, 46 (2007) 1083-1089. From the MFR of the total polymer and the MFR of the XS fraction, the MFR of the matrix component of an impact copolymer can be calculated using a logarithmic mixing rule, i.e. assuming the validity of the following equation:

$$MFR(Total) = 10^{(1-w(EPR))\log 10(MFR(Matrix)) + w(EPR)\log 10(MFR(XCS))}$$

with w(EPR) being the weight fraction of the elastomeric phase, approximated by the weight fraction of the XS.

Intrinsic viscosity is measured according to DIN ISO 1628/1 and /3, October 1999 (in Decalin at 135° C.). The intrinsic viscosity (IV) value increases with the molecular weight of a polymer.

Glass Transition Temperature

The glass transition temperature Tg is determined by dynamic mechanical analysis according to ISO 6721-7. The measurements are done in torsion mode on compression moulded samples (40×10×1 mm$^3$) between −100° C. and +150° C. with a heating rate of 2° C./min and a frequency of 1 Hz.

GPC:

Molecular weight averages, molecular weight distribution, and polydispersity index ($M_n$, $M_w$, $M_w/M_n$)

Molecular weight averages (Mw, Mn), Molecular weight distribution (MWD) and its broadness, described by polydispersity index, PDI=Mw/Mn (wherein Mn is the number average molecular weight and Mw is the weight average molecular weight) were determined by Gel Permeation Chromatography (GPC) according to ISO 16014-4:2003 and ASTM D 6474-99. A Waters GPCV2000 instrument, equipped with differential refractive index detector and online viscosimeter was used with 2×GMHXL-HT and 1×G7000HXL-HT TSK-gel columns from Tosoh Bioscience and 1,2,4-trichlorobenzene (TCB, stabilized with 250 mg/L 2,6-Di tert butyl-4-methyl-phenol) as solvent at 140° C. and at a constant flow rate of 1 mL/min. 209.5 μL of sample solution were injected per analysis. The column set was calibrated using universal calibration (according to ISO 16014-2:2003) with at least 15 narrow MWD polystyrene (PS) standards in the range of 1 kg/mol to 12 000 kg/mol. Mark Houwink constants for PS, PE and PP used are as per ASTM D 6474-99. All samples were prepared by dissolving 0.5-4.0 mg of polymer in 4 mL (at 140° C.) of stabilized TCB (same as mobile phase) and keeping for max. 3 hours at max. 160° C. with continuous gentle shaking prior sampling into the GPC instrument.

Determination of Xylene Soluble Fraction (XS):

The xylene soluble fraction (XS) as defined and described in the present invention is determined as follows: 2.0 g of the polymer were dissolved in 250 ml p-xylene at 135° C. under agitation. After 30 minutes, the solution was allowed to cool for 15 minutes at ambient temperature and then allowed to settle for 30 minutes at 25±0.5° C. The solution was filtered with filter paper into two 100 ml flasks. The solution from the first 100 ml vessel was evaporated in nitrogen flow and the residue dried under vacuum at 90° C. until constant weight is reached. The xylene soluble fraction (percent) can then be determined as follows:

$$XS\% = (100 \times m1 \times v0)/(m0 \times v1),$$

wherein m0 designates the initial polymer amount (grams), m1 defines the weight of residue (grams), v0 defines the initial volume (milliliter) and v1 defines the volume of the analysed sample (milliliter).

Ethylene Content (FTIR $C_2$)

Ethylene content was measured with Fourier transform infrared spectroscopy (FTIR) calibrated to results obtained by $^{13}$C NMR spectroscopy using a method which accounts for regio-irregular propene insertion. When measuring the ethylene content in polypropylene, a thin film of the sample (thickness about 0.220 to 0.250 mm) was prepared by hotpressing at 230° C. (preheat 5 min., press 1 min., cooling (cold water) 5 min.) using a Graseby Specac press. The FTIR spectra of the sample was recorded immediately with Nicolet Protégé 460 spectrometer from 4000 to 400 cm$^{-1}$, resolution 4 cm$^{-1}$, scans 64. The area of absorption peak at 733 cm$^{-1}$ (baseline from 700 cm$^{-1}$ to 760 cm$^{-1}$) and height of reference peak at 809 cm$^{-1}$ (baseline from 780 cm$^{-1}$ to 880 cm$^{-1}$) were evaluated. The result was calculated using the following formula $$E_{tot} = a \times A/R + b$$

where
A=area of absorption peak at 733 cm$^{-1}$
R=height of reference peak at 809 cm$^{-1}$
$E_{tot}$=C2 content (wt.-%)
a, b are calibration constants determined by correlation of multiple
calibration standards of know ethylene content as determined by $^{13}$C NMR spectroscopy to A/R.

The result was reported as an average of two measurements.

DMTA

The dynamic-mechanical analysis (DMTA) data are obtained according to ISO 6721-1 (General principles) & 6721-7 (Torsional vibration-Non-resonance method)

Experimental Setup:

A Rheometric scientific ARES rheometer, equipped with a liquid nitrogen unit and an oven (convection and radiation heating), a standard torsion rectangular tool and a software orchestrator V6.5.8, or Anton Paar MCR301 rheometer with a TC30 temperature control unit combined with a liquid nitrogen unit and an CTD600 oven (convection and radiation heating) a standard torsion rectangular tool and a software RHEOPLUS/32 v3.40 are used.

Sample Preparation

Stabilized dry pellets are compression molded at 210° C. (gel time 5 min, pressure time 25 bar/3 min, cooling rate 25 bar/15K/min, de-molding temperature 40° C.) in a 100*100*1 mm mould. Only from homogeneous, bubble free plates are punched to 50×10×1 mm stripes and are conditioned at least 96 hours at room temperature.

Conducting the Experiment:

The device is cooled with the clamped sample to the initial temperature (standard −130° C.). After 5 min delay time the experiment is started with a test frequency of 1 Hz, a heating rate of 2K/min and a strain ε of 0.1%. The measurements are carried out under inert atmosphere (nitrogen) and a tension (vertically) force of 50 g (+/−20 g).

Temperature dependence of storage modulus G', loss modulus G", and loss angle tangent tan(δ) are used for evaluations.

Determinations of transition sections (e.g. glass transition temperature, $T_g$) is based on the loss tangent tan(δ) vs. temperature curve (peak of the curve).

Number of specimen: 1. Precision: +/−5%, temperature values: +/−1.5K

Charpy Notched Impact Strength

Charpy impact strength was determined according to ISO 179-1eA:2000 on V-notched samples of 80×10×4 mm$^3$ at 23° C. (Charpy impact strength (23° C.)) and −20° C. (Charpy impact strength (−20° C.)). A standard impact velocity of 2.9 m/s was used.

The test specimens having a dimension of 80×10×4 mm$^3$ were cut from the central part of ISO multibar specimens prepared by injection moulding in line with ISO 1872-2.

Brittle-to-Ductile Transition Temperature

The determination of the brittle-to-ductile transition temperature (BDTT) is based on the a(cN) values as determined from Charpy instrumented impact strength according to ISO 179-2:2000 on V-notched specimen with a geometry of 80×10×4 mm3 as required in ISO 179-1eA.

The a(cN) values are determined in intervals of 3° C. from −40° C. to +41° C. with an impact velocity of 1.5 m/s and plotted over temperature, calculating the BDTT as the average value of the step increase. For a detailed description of the determination of the BDTT reference is made to Grein, C. et al, Impact Modified Isotactic Polypropylene with Controlled Rubber Intrinsic Viscosities: Some New Aspects About Morphology and Fracture, J Appl Polymer Sci, 87 (2003), 1702-1712.

Tensile Modulus and Strain at Break

Tensile properties were determined according to ISO 527-2 (cross head speed=50 mm/min; 23° C.) using injection moulded specimens as described in EN ISO 1873-2 (dog bone shape, 4 mm thickness).

EXAMPLES

Chemicals

All the chemicals and chemical reactions were handled under an inert gas atmosphere using Schlenk and glovebox techniques, with oven-dried glassware, syringes, needles or cannulas.

MAO was purchased from Albermarle and used as a 30 wt-% solution in toluene. Perfluoroalkylethyl acrylate ester mixture (CAS number 65605-70-1) was purchased from the Cytonix corporation, dried over activated molecular sieves (2 times) and degassed by argon bubbling prior to use. Hexadecafluoro-1,3-dimethylcyclohexane (CAS number 335-27-3) was obtained from commercial sources and dried over activated molecular sieves (2 times) and degassed by argon bubbling prior to use. Triethylaluminum was purchased from Crompton and used in pure form. Hydrogen is provided by AGA and purified before use. Propylene is provided by Borealis and adequately purified before use.

1-tert-Butyl-2-methoxybenzene was synthesized via alkylation of 2-tert-butylphenol (Acros) by dimethylsulfate (Merck) in the presence of aqueous NaOH (Reachim, Russia) as described in [Stork, G.; White, W. N. *J. Am. Chem. Soc.* 1956, 78, 4604.]. 2-Methyl-4-bromo-6-tert-butylindanone-1 was obtained as described in the literature [Resconi, L.; Nifant'ev, I. E.; Ivchenko, P. V.; Bagrov, V.; Focante, F.; Moscardi, G. Int. Pat. Appl. WO2007/107448 A1].

7-Bromo-5-tert-butyl-2-methyl-1H-indene was obtained from 2-methyl-4-bromo-6-tert-butylindanone-1 as described in [Voskoboynikov, A. Z.; Asachenko, A. F.; Kononovich, D. S.; Nikulin M. V.; Tsarev, A. A.; Maaranen, J.; Vanne, T.; Kauhanen, J.; Mansner, E.; Kokko, E.; Saarinen, L. Int. Pat. Appl. WO2009/027075].

Bis(2,6-diisopropylphenyl)imidazolium chloride, i.e. IPr (HCl), and (IPr)NiCl$_2$(PPh$_3$) were synthesized as described in [Hintermann, L. *Beilstein J. Org. Chem.* 2007, 3, 1.] and [Matsubara, K.; Ueno, K.; Shibata, Y. *Organometallics* 2006, 25, 3422.], respectively.

4/7-Bromo-2-methyl-3/1/H-indene was obtained as described in [Izmer, V. V.; Lebedev, A. Y.; Nikulin, M. V.; Ryabov, A. N.; Asachenko, A. F.; Lygin, A. V.; Sorokin, D. F.; Voskoboynikov, A. Z. *Organometallics* 2006, 25, 1217.].

Anisole (Acros), 3-methylanisole (Acros), tert-Butyltoluene (Aldrich), 1-Bromo-4-tert-butylbenzene (Acros), P$_4$O$_{10}$ (Reachim), Pd(P$^t$Bu$_3$)$_2$ (Strem), 1.0 M ZnCl$_2$ in THF (Aldrich), 1.0 M 3,5-di-tert-butylphenylmagnesium bromide in THF (Aldrich), hexanes (Reachim, Russia), N-bromosuccinimide (Acros), diethyl methylmalonate (Aldrich), methyl iodide (Acros), acetone (Reachim, Russia), tetraethylammonium iodide (Acros), triphenylphosphine (Acros), CuCN (Merck), methanesulfonic acid (Aldrich), sodium tetraphenylborate (Aldrich), palladium acetate (Aldrich), copper cyanide (Merck), magnesium turnings (Acros), lithium aluminiumhydride (Aldrich), bromobenzene (Acros), 2.5 M "BuLi in hexanes (Chemetall), ZrCl$_4$(THF)$_2$ (Aldrich), NaBH$_4$ (Aldrich), Ni(OAc)$_2$ (Aldrich), silica gel 60 (40-63 um, Merck), AlCl$_3$ (Merck), bromine (Merck), benzoyl peroxide (Aldrich), iodine (Merck), NaHCO$_3$ (Merck), Na$_2$CO$_3$ (Merck), K$_2$CO$_3$ (Merck), Na$_2$SO$_4$ (Merck), Na$_2$SO$_3$ (Merck), sodium metal (Merck), thionyl chloride (Merck), sodium acetate, trihydrate (Merck), tetraethylammonium iodide (Acros), triphenylphosphine (Acros), KOH (Merck), Na$_2$SO$_4$ (Akzo Nobel), TsOH (Aldrich), 12 M HCl (Reachim, Russia), methanol (Merck), anhydrous ethanol (Merck), CDCl$_3$ and DMSO-d$_6$ (Deutero GmbH) as well as hexanes (Merck), carbon tetrachloride (Merck), ether (Merck), ethyl acetate (Merck), toluene (Merck) and CH$_2$Cl$_2$ (Merck) for extractions were used as received.

Tetrahydrofurane (Merck), ether (Merck), and dimethoxyethane (Acros) freshly distilled from benzophenone ketyl were used. Dichloromethane (Merck) for organometallic synthesis as well as CD$_2$Cl$_2$ (Deutero GmbH) for NMR experiments were dried and kept over CaH$_2$. Toluene (Merck), n-octane (Merck), and hexanes (Merck) for organometallic synthesis were kept and distilled over Na/K alloy. Dichlorodimethylsilane (Merck) and methacrylic acid (Acros) were distilled before use.

Rac-methyl(cyclohexyl)silanediylbis[2-methyl-4-(4-tert-butylphenyl)indenyl]zirconium dichloride (C1)

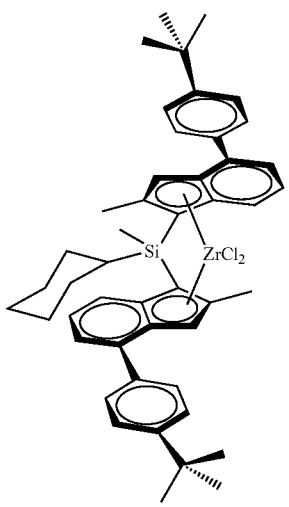

was purchased from a commercial source.

Rac-dimethylsilanediylbis(2-methyl-4-phenyl-5-methoxy-6-tert-butylindenyl) zirconium dichloride (C2)

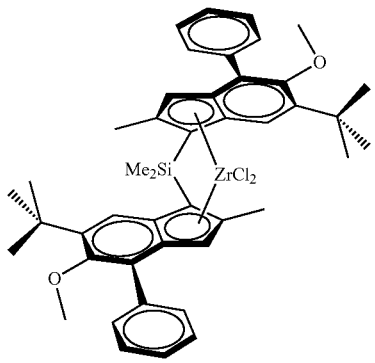

was synthesized as described in WO 2007/116034.

Preparation of Example Metallocene Complexes

Synthesis of anti-Dimethylsilylene(2-methyl-4-phenyl-5-methoxy-6-tert-butyl-indenyl)(2-methyl-4-phenyl-6-tert-butyl-indenyl)zirconium dichloride Metallocene E1

6-tert-Butyl-5-methoxy-2-methylindan-1-one

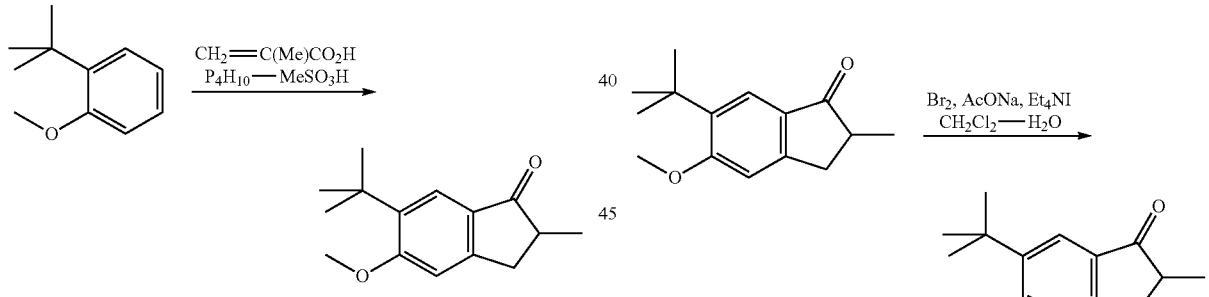

To an Eaton's reagent obtained from 110 g of $P_4O_{10}$ and 560 ml of methanesulfonic acid a mixture of 65.6 g (0.399 mol) of 1-tert-butyl-2-methoxybenzene and 43.0 g (0.50 mol) of methacrylic acid was added for ca. 1 h at 50-55° C. The resulting mixture was stirred for 1 h at this temperature, then cooled to room temperature, and poured on a mixture of 1 liter of cold water and 1 kg of ice. The crude product was extracted with 3×500 ml of dichloromethane. The combined organic extract was washed by aqueous $K_2CO_3$ and then evaporated to dryness. Fractional rectification of the residue gave 64.9 g of yellowish oil which crystallizes at room temperature. On the evidence of NMR spectroscopy, this product includes ca. 90% of the target material. Further on, this product was dissolved in 180 ml of hot hexanes. Crystals precipitated from this solution at room temperature were collected, washed by 100 ml of cold hexanes, and dried in vacuum. This procedure gave 39.6 g (43%) of the analytically pure substituted indanone.

Anal. calc. for $C_{15}H_{20}O_2$: C, 77.55; H, 8.68. Found: C, 77.48; H, 8.79.

$^1$H NMR (CDCl$_3$): δ 7.68 (s, 1H, 7-H in indanone), 6.87 (s, 1H, 4-H in indanone), 3.93 (s, 3H, OMe), 3.32 (m, 1H, 3-H in indanone), 2.69 (m, 1H, 2-H in indanone), 2.64 (m, 1H, 3'-H in indanone), 1.37 (s, 9H, $^t$Bu), 1.29 (d, J=7.3 Hz, 3H, 2-Me in indanone). $^{13}$C {$^1$H} NMR (CDCl$_3$): δ 208.1, 164.6, 154.4, 138.8, 128.7, 122.1, 107.8, 55.2, 42.1, 35.0, 34.7, 29.6, 16.6.

6-tert-Butyl-5-methoxy-2-methylindan-1-one (second experiment)

To Eaton's reagent obtained from 118 g of $P_4O_{10}$ and 600 ml of methanesulfonic acid a mixture of 70.3 g (0.428 mol) of 1-tert-butyl-2-methoxybenzene and 295.0 g (3.43 mol, 8 eqv.) of methacrylic acid was added for ca. 1 h at 50-55° C. The resulting mixture was stirred for 0.5 h at this temperature, then cooled to room temperature, and poured on a mixture of 1.5 liter of cold water and 2 kg of ice. After the ice melts, the precipitated crude 6-tert-butyl-5-methoxy-2-methylindan-1-one was filtered off and then washed with 2×100 ml of cold water. The crude product was dissolved in 500 ml of dichloromethane, and this solution was washed by aqueous $K_2CO_3$, dried over anhydrous $K_2CO_3$, and then evaporated on Rotavap. The residue was distilled in vacuum to give 70.6 g of crude 6-tert-butyl-5-methoxy-2-methylindan-1-one, b.p. 155-165° C./5 mm Hg. This product was dissolved in 200 ml of hot hexanes. Crystals precipitated from this solution at 5° C. were collected, washed by 50 ml of cold hexanes, and dried in vacuum. This procedure gave 64.1 g (65%) of the analytically pure substituted indanone.

4-Bromo-6-tert-butyl-5-methoxy-2-methylindan-1-one

To a mixture of 60.0 g (0.258 mol) of 6-tert-butyl-5-methoxy-2-methylindan-1-one, 130 g of NaOAc(H$_2$O)$_3$, 1.5 g of Et$_4$NI, 220 ml of dichloromethane, and 450 ml of water cooled to 5° C. 45.0 g (0.282 mol) of bromine was added for ca. 5 min by vigorous stirring. This mixture was stirred for 1 h at 5° C., and then a solution of 60.0 g of NaOAc(H$_2$O)$_3$ in 200 ml of water was added. To the resulting mixture 23.5 (0.147 mmol) of bromine was added at 5° C. The resulting solution was stirred for 30 min and then Na$_2$SO$_3$ was added by small portions to remove an excess of bromine. The CH$_2$Cl$_2$-layer was separated from the top aqueous one and the latter was extracted with 2×300 ml of dichloromethane. The combined organic extract was dried over K$_2$CO$_3$, passed through a short layer of silica gel 60 (40-63 um) and then evaporated to dryness. The residue was dried in vacuum to give 79.9 g (99%) of the title compound which was further used without an additional purification.

Anal. calc. for $C_{15}H_{19}BrO_2$: C, 57.89; H, 6.15. Found: C, 57.70; H, 6.08.

$^1$H NMR (CDCl$_3$): δ 7.70 (s, 1H, 7-H in indanone), 4.03 (s, 3H, OMe), 3.31 (dd, J=17.4 Hz, J=7.8 Hz, 1H, 3-H in indanone), 2.72 (m, 1H, 2-H in indanone), 2.62 (dd, J=17.4 Hz, J=3.8 Hz, 1H, 3'-H in indanone), 1.40 (s, 9H, $^t$Bu), 1.32 (d, J=7.6 Hz, 3H, 2-Me in indanone). $^{13}$C {$^1$H} NMR (CDCl$_3$): δ 208.0, 162.8, 154.0, 145.5, 132.7, 121.5, 116.7, 61.7, 42.2, 36.1, 35.7, 30.6, 16.4.

6-tert-Butyl-5-methoxy-2-methyl-4-phenylindan-1-one

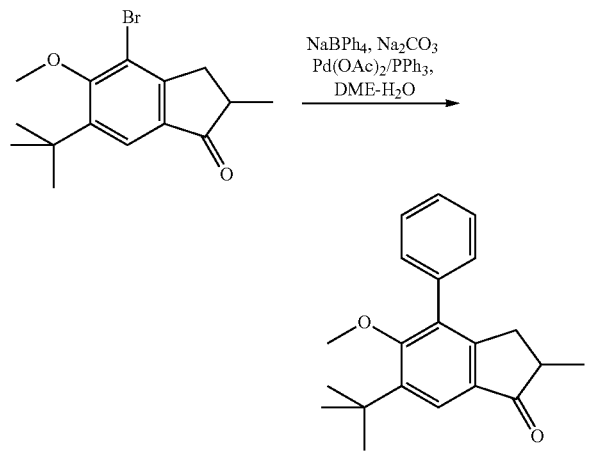

To a mixture of 46.7 g (0.150 mol) of 4-bromo-6-tert-butyl-5-methoxy-2-methylindan-1-one, 44.0 g (0.415 mol) of Na$_2$CO$_3$, 25.7 g (0.075 mol) of NaBPh$_4$, 600 ml of DME, and 240 ml of water 1.01 g (4.50 mmol) of Pd(OAc)$_2$ and 2.36 g (9.00 mmol) of PPh$_3$ were added. The resulting mixture was refluxed for 12 h, cooled to room temperature, and then evaporated to dryness. To the residue 1 liter of cold water was added, and the crude product was extracted with 3×300 ml of dichloromethane. The combined organic extract was dried over K$_2$CO$_3$ and then evaporated to dryness. The product was isolated by flash chromatography on silica gel 60 (40-63 um; eluent: hexanes-dichloromethane-ether=20:10:1, vol.). Yield 46.0 g (99%) of yellowish crystalline solid.

Anal. calc. for $C_{21}H_{24}O_2$: C, 81.78; H, 7.84. Found: C, 81.90; H, 7.93.

$^1$H NMR (CDCl$_3$): δ 7.76 (s, 1H, 7-H in indanone), 7.47 (m, 2H, 3,5-H in Ph), 7.42 (m, 2H, 2,6-H in Ph), 7.39 (m, 1H, 4-H in Ph), 3.29 (s, 3H, OMe), 3.13 (dd, J=17.4 Hz, J=7.8 Hz, 1H, 3-H in indanone), 2.63 (m, 1H, 2-H in indanone), 2.47 (dd, J=17.4 Hz, J=3.8 Hz, 1H, 3'-H in indanone), 1.43 (s, 9H, $^t$Bu), 1.25 (d, J=7.3 Hz, 3H, 2-Me in indanone). $^{13}$C {$^1$H} NMR (CDCl$_3$): δ 208.7, 163.5, 152.7, 143.5, 136.4, 132.5, 131.0, 129.5, 128.7, 127.5, 121.6, 60.5, 42.2, 35.4, 34.3, 30.5, 16.4.

6-tert-Butyl-5-methoxy-2-methyl-4-phenylindan-1-one (second experiment)

To a mixture of 46.7 g (0.150 mol) of 4-bromo-6-tert-butyl-5-methoxy-2-methylindan-1-one, 44.5 g (0.420 mol) of Na$_2$CO$_3$, 22.0 g (0.180 mol) of PhB(OH)$_2$, 570 ml of DME, and 195 ml of water 0.674 g (3.0 mmol) of Pd(OAc)$_2$ and 1.58 g (6.00 mmol) of PPh$_3$ were added. The resulting mixture was refluxed for 12 h, cooled to room temperature, and then DME was evaporated on Rotavap. To the residue 1 liter of cold water was added, and the crude product was extracted with 3×300 ml of dichloromethane. The combined organic extract was dried over K$_2$CO$_3$ and then evaporated to dryness. The residue after evaporation was extracted with hot hexane (500 ml, then 3×250 ml) and this extracts while hot were passed through a short pad of silicagel, evaporated on Rotavap to yield 45.1 g (98%) of 6-tert-butyl-5-methoxy-2-methyl-4-phenylindan-1-one as a slightly yellowish crystalline solid which was further used without an additional purification.

5-tert-Butyl-6-methoxy-2-methyl-7-phenyl-1H-indene

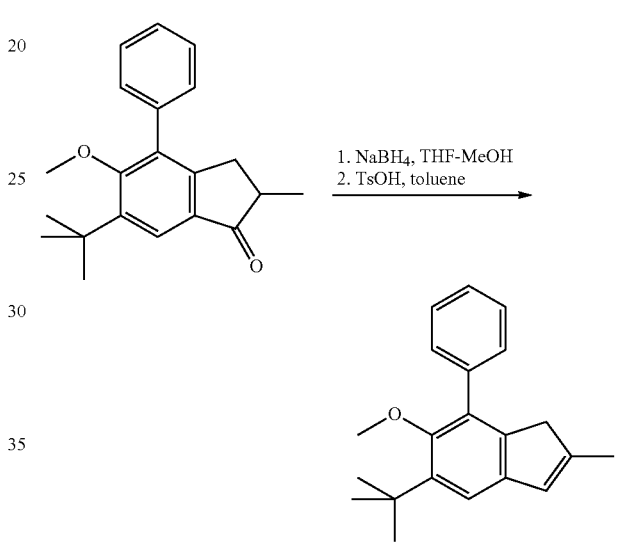

To a solution of 45.9 g (0.149 mmol) of 6-tert-butyl-5-methoxy-2-methyl-4-phenylindan-1-one in 300 ml of THF cooled to 5° C. 8.51 g (0.225 mol) of NaBH$_4$ was added. Further on, 150 ml of methanol was added dropwise to this mixture by vigorous stirring for ca. 7 h at 5° C. The resulting mixture was stirred overnight at room temperature, and then 1 liter of cold water and 12 M HCl to pH~1 were added. The crude product was extracted with 3×200 ml of dichloromethane, the combined organic extract was dried over K$_2$CO$_3$ and then evaporated to dryness. To a solution of the residue in 800 ml of toluene 1.0 g of TsOH was added, this mixture was refluxed with Dean-Stark head for 10 min and then cooled to room temperature using water bath. The resulting solution was washed by 10% aqueous Na$_2$CO$_3$, the organic layer was separated, the aqueous layer was extracted with 2×50 ml of dichloromethane. The combined organic solution was dried over K$_2$CO$_3$ and then passed through short layer of silica gel 60 (40-63 um). The silica gel layer was additionally washed by 100 ml of dichloromethane. The combined organic elute was evaporated to dryness. This procedure gave 43.1 g (99%) of yellowish oil which was further used without an additional purification.

Anal. calc. for $C_{21}H_{24}O$: C, 86.26; H, 8.27. Found: C, 86.39; H, 8.37.

$^1$H NMR (CDCl$_3$): δ 7.47-7.49 (m, 2H, 2,6-H in Ph), 7.43 (m, 2H, 3,5-H in Ph), 7.34 (m, 1H, 4-H in Ph), 7.22 (s, 1H, 4-H in indene), 6.44 (m, 1H, 3-H in indene), 3.22 (s, 3H, OMe), 3.12 (s, 2H, 1,1'-H in indene), 2.06 (s, 3H, 2-Me in indene), 1.44 (s, 9H, $^t$Bu). $^{13}$C{$^1$H} NMR (CDCl$_3$): δ 154.3, 145.3, 141.7, 141.0, 138.5, 131.6, 129.5, 128.3, 126.9, 126.8, 117.2, 60.7, 42.8, 35.2, 31.0, 16.6.

5-tert-Butyl-6-methoxy-2-methyl-7-phenyl-1H-indene (second experiment)

To a solution of 44.3 g (0.144 mmol) of 6-tert-butyl-5-methoxy-2-methyl-4-phenylindan-1-one in 150 ml of THF cooled to 5° C. 2.72 g (71.9 mmol) of NaBH$_4$ was added. Further on, 75 ml of methanol was added dropwise to this mixture by vigorous stirring for 1 h at 5° C. The resulting mixture was stirred additionally 1 h at 5° C., then 0.5 h at room temperature, and then added to 1 liter of cold water and 30 ml of 12 M HCl in separating funnel. The crude product was extracted consequentially with 250, 100 and 50 ml of dichloromethane, and the combined organic extract was evaporated to dryness. To a solution of the residue in 500 ml of toluene 1.0 g of TsOH was added, this mixture was refluxed with Dean-Stark head for 10 min and then cooled to room temperature using water bath. The resulting solution was washed by aqueous K$_2$CO$_3$ (20 g K$_2$CO$_3$ in 200 ml of H$_2$O), the organic layer was separated, the aqueous layer was extracted with 2×50 ml of dichloromethane. The combined organic solution was dried over K$_2$CO$_3$ and then passed through short layer of silica gel 60 (40-63 um, ca. 10 g). The silica gel layer was additionally washed by 50 ml of dichloromethane. The combined organic elute was evaporated to dryness. This procedure gave 42.0 g (~100%) of yellowish oil which was further used without an additional purification.

(6-tert-Butyl-5-methoxy-2-methyl-4-phenyl-1H-inden-1-yl)(chloro)dimethylsilane

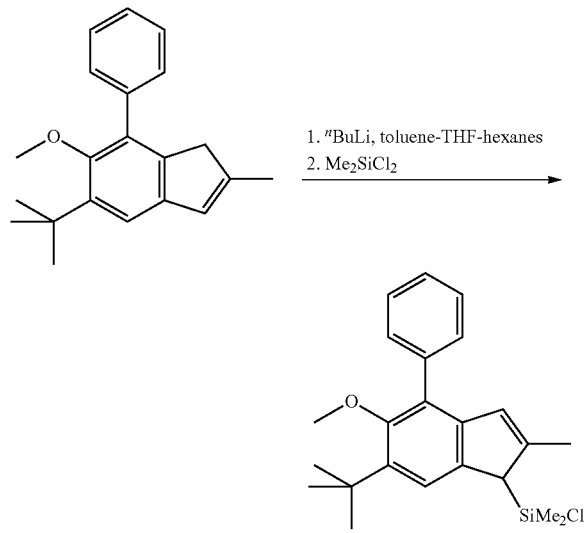

To a solution of 16.2 g (55.4 mmol) of 5-tert-butyl-6-methoxy-2-methyl-7-phenyl-1H-indene in 300 ml of toluene, 22.2 ml (55.5 mmol) of 2.5 M $^n$BuLi in hexanes was added at room temperature. The resulting viscous solution was stirred for 2 h, and then 15 ml of THF was added. The formed suspension was stirred for 12 h at room temperature, ca. 2 h at 60° C., then cooled to −20° C., and 35.8 g (277 mmol) of dichlorodimethylsilane was added in one portion. The resulting solution was warmed to 60° C. and stirred for 1 h at this temperature. The resulting mixture was evaporated to ca. ½ of its volume, then filtered through glass frit (G3). The precipitate was additionally washed by 20 ml of toluene. The combined filtrate was evaporated to dryness to give 21.2 g (99%) of viscous yellowish oil.

Anal. calc. for C$_{23}$H$_{29}$ClOSi: C, 71.75; H, 7.59. Found: C, 71.92; H, 7.80.

$^1$H NMR (CDCl$_3$): δ 7.52-7.54 (m, 2H, 2,6-H in Ph), 7.48 (m, 2H, 3,5-H in Ph), 7.45 (s, 1H, 7-H in indenyl), 7.38 (m, 1H, 4-H in Ph), 6.49 (m, 1H, 3-H in indenyl), 3.59 (m, 1H, 1-H in indenyl), 3.27 (s, 3H, OMe), 2.23 (m, 3H, 2-Me in indenyl), 1.48 (s, 9H, $^t$Bu), 0.47 (s, 3H, SiMeMe'), 0.22 (s, 3H, SiMeMe'). $^{13}$C{$^1$H} NMR (CDCl$_3$): δ 155.8, 146.2, 143.7, 138.2, 137.6, 137.0, 130.2, 128.3, 127.4, 126.7, 126.5, 121.1, 60.5, 50.1, 35.2, 31.2, 17.6, 1.1, −0.6.

5-tert-Butyl-2-methyl-7-phenyl-1H-indene

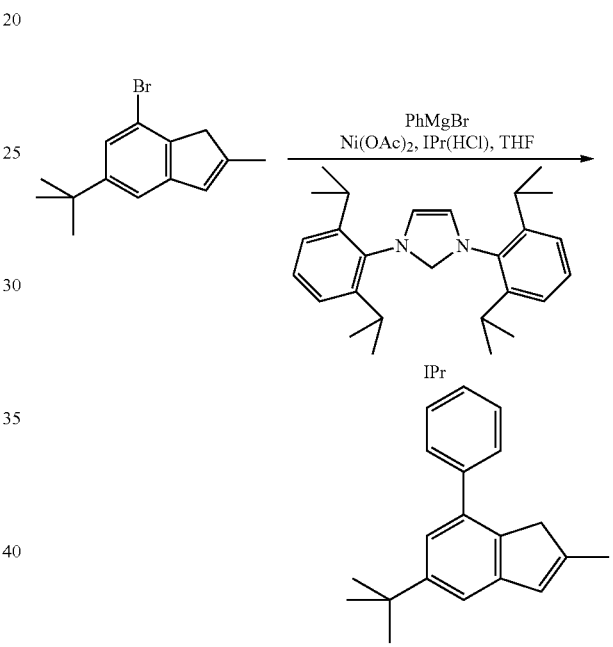

To a solution of PhMgBr obtained from 89.0 g (567 mmol) of bromobenzene, 15.8 g (650 mmol) of magnesium turnings and 450 ml of THF, 1.60 g (3.76 mmol) of bis(2,6-diisopropylphenyl)imidazolium chloride, i.e. IPr(HCl) and 0.66 g (3.76 mmol) of Ni(OAc)$_2$ were added. Further on, a solution of 50.0 g (189 mmol) of 7-bromo-5-tert-butyl-2-methyl-1H-indene in 50 ml of THF was added. The resulting mixture was stirred for 2 h at room temperature, refluxed for 1 h, cooled to ambient temperature, and then 200 ml of water was added dropwise. Finally, 100 ml of 12 M HCl was added dropwise. The product was extracted with 300 ml of ether. The organic layer was separated, and the aqueous layer was additionally extracted with 2×150 ml of dichloromethane. The combined organic extract was dried over K$_2$CO$_3$, passed through a short layer of silica gel 60 (40-63 um), and then evaporated to dryness. Fractional rectification of the residue gave 34.7 g (70%) of viscous yellow oil, b.p. 180-210° C./5 mm Hg. The product is a ca. 1 to 1 mixture of 6-tert-butyl-2-methyl-4-phenyl-1H-indene and 5-tert-butyl-2-methyl-7-phenyl-1H-indene.

Anal. calc. for C$_{20}$H$_{22}$: C, 91.55; H, 8.45. Found: C, 91.61; H, 8.50.

$^1$H NMR (CDCl$_3$): δ 7.52 (m, 4H), 7.40-7.43 (m, 6H), 7.29-7.33 (m, 3H), 7.17 (m, 1H), 6.62 (m, 1H), 6.50 (m, 1H), 3.32 (s, 4H), 2.10 (s, 6H), 1.37 (s, 9H), 1.36 (s, 9H).

(6-tert-Butyl-5-methoxy-2-methyl-4-phenyl-1H-inden-1-yl)-(6-tert-butyl-2-methyl-4-phenyl-1H-inden-1-yl)dimethylsilane

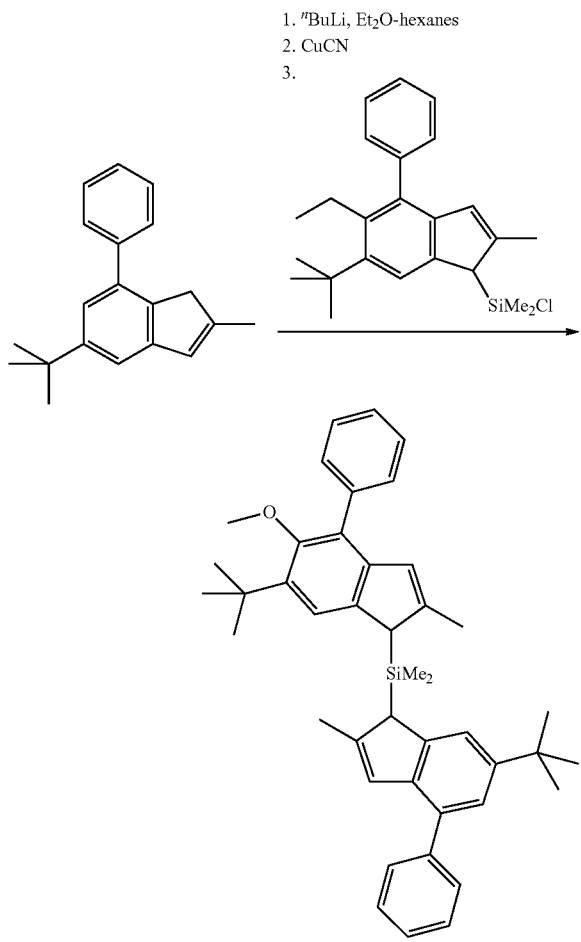

To a solution of 14.5 g (55.4 mmol) of 5-tert-butyl-2-methyl-7-phenyl-1H-indene in 400 ml of ether cooled to −78° C., 22.2 ml (55.5 mmol) of 2.5 M $^n$BuLi in hexanes was added. This mixture was stirred overnight at room temperature, then cooled to −78° C., and 200 mg (2.23 mmol) of CuCN was added. The resulting mixture was stirred for 30 min at −20° C., then cooled to −78° C., and a solution of 21.2 g (55.4 mmol) of (6-tert-butyl-5-methoxy-2-methyl-4-phenyl-1H-inden-1-yl)(chloro)dimethylsilane in 200 ml of ether was added. This mixture was stirred overnight at room temperature, then 1 ml of water was added. The obtained mixture was passed through a short layer of silica gel 60 (40-63 um), the elute was evaporated to dryness. The product was isolated by flash-chromatography on silica gel 60 (40-63 um; eluent: hexanes-dichloromethane=10:1, vol., then 3:1, vol.). This procedure gave 24.5 g (72%) of yellowish glassy solid.

Anal. calc. for C$_{43}$H$_{50}$OSi: C, 84.54; H, 8.25. Found: C, 84.69; H, 8.34.

$^1$H NMR (CDCl$_3$): δ 7.35-7.62 (m), 6.81 (s), 6.75 (s), 6.63 (s), 6.45 (s), 3.73 (s), 3.71 (s), 3.70 (s), 3.30 (s), 2.23 (s), 2.22 (s), 2.15 (s), 2.08 (s), 1.50 (s), 1.49 (s), 1.43 (s), 1.42 (s), 0.06 (s), −0.06 (s), −0.07 (s), −0.08 (s), −0.12 (s).

Anti-Dimethylsilylene(2-methyl-4-phenyl-5-methoxy-6-tert-butyl-indenyl)(2-methyl-4-phenyl-6-tert-butyl-indenyl)zirconium dichloride (metallocene E1)

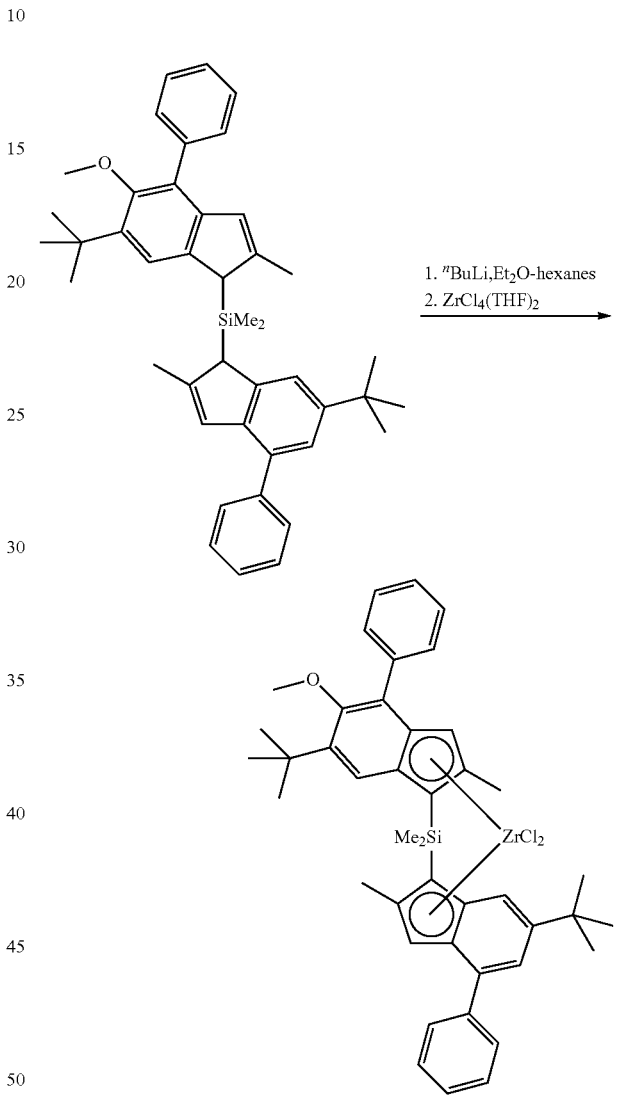

To a solution of 7.64 g (12.5 mmol) of (6-tert-butyl-5-methoxy-2-methyl-4-phenyl-1-inden-1-yl)(6-tert-butyl-2-methyl-4-phenyl-1H-inden-1-yl) dimethylsilane in 200 ml of ether cooled to −78° C., 10.0 ml (25.0 mmol) of 2.5 M $^n$BuLi in hexanes was added. The resulting mixture was stirred overnight at room temperature, then cooled to −78° C., and 4.72 g (12.5 mmol) of ZrCl$_4$(THF)$_2$ was added. This mixture was stirred for 24 h at room temperature. On the evidence of NMR spectroscopy, this mixture included anti and syn zirconocenes in ratio equal to ca. 70:30. This mixture was filtered through glass frit (G4), the filtrate was evaporated to dryness. The residue was dissolved in a mixture of 60 ml of n-octane and 15 ml of toluene at reflux. Crystals precipitated from this solution at −30° C. were collected, washed by 2×10 ml of cold hexanes, and dried in vacuum. This procedure gave 1.97 g (20%) of pure racemic-anti zirconocene. Additional amount of this product was obtained in similar manner from the mother liquid. Thus, the combined yield of the product was 3.54 g (37%) as yellowish-orange crystalline solid.

Anal. calc. for $C_{43}H_{48}Cl_2OSiZr$: C, 66.98; H, 6.27. Found: C, 67.09; H, 6.33.

$^1$H NMR (CDCl$_3$): δ 7.28-7.70 (m, 13H, 7-H and 5,7-H in indenyls and Ph), 6.94 (s, 1H, 3-H in indenyl), 6.60 (s, 1H, 3-H in indenyl), 3.41 (s, 3H, OMe), 2.26 (s, 3H, 2-Me in indenyl), 2.23 (s, 3H, 2-Me in indenyl), 1.42 (s, 9H, $^t$Bu), 1.36 (s, 3H, SiMeMe'), 1.35 (s, 9H, $^t$Bu), 1.34 (s, 3H, SiMeMe').

Synthesis of anti-dimethylsilylene(2-methyl-4-phenyl-5-methoxy-6-tert-butyl-indenyl)(2-methyl-4-(4-tert-butyl-phenyl)indenyl)zirconium dichloride Metallocene E2

4/7-(4-tert-Butylphenyl)-2-methyl-3/1H-indene

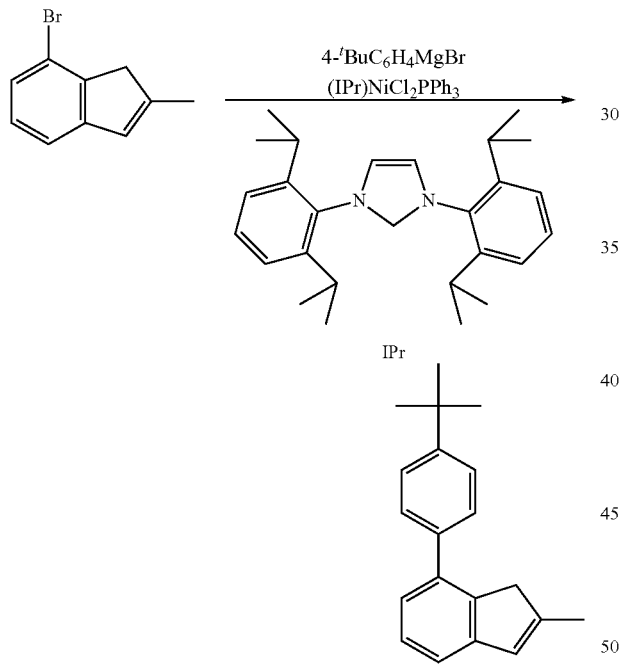

To a solution of 4-tert-butylphenylmagnesium bromide obtained from 110 g (0.518 mol) of 1-bromo-4-tert-butyl-benzene and 12.6 g (0.518 mol) of magnesium turnings in 500 ml of THF, 0.65 g (0.83 mmol) (IPr)NiCl$_2$PPh$_3$ and a solution of 77.6 g (0.371 mol) of 4/7-bromo-2-methyl-3/1H-indene in 50 ml of THF were added. This mixture was stirred at reflux for 30 min, and then for 20 min at room temperature. Finally, 150 ml of water and then 70 ml of 4 M HCl were added. The product was extracted with 200 ml of ether and then 2×100 ml of dichloromethane. The combined organic extract was dried over K$_2$CO$_3$, passed through a short column with Silica Gel 60, and evaporated to dryness. Rectification of the residue, b.p. 163-171° C./5 mm Hg, gave 93.8 g (96%) of a mixture of the title isomeric indenes as yellowish viscous oil which is slowly crystallized.

Anal. calc. for $C_{20}H_{22}$: C, 91.55; H, 8.45. Found: C, 91.62; H, 8.52.

$^1$H NMR (CDCl$_3$): δ 7.62 (m, C$_6$H$_4$ of both isomers), 7.46 (m, 5- and 6-H in 4- and 7-arylindenes), 7.40 (m, 7- and 4-H in 4- and 7-arylindenes), 7.31 (m, 6- and 5-H in 4- and 7-arylindenes), 6.88 (m, 3-H in 4/7-arylindene), 6.68 (m, 3-H in 7/4-arylindene), 3.55 (m, 1-CH$_2$ in 7/4-arylindene), 3.49 (m, 1-CH$_2$ in 4/7-arylindene), 2.28 (2-Me in 4/7-arylindene), 2.27 (2-Me in 7/4-arylindene), 1.54 (s, $^t$Bu in 4- and 7-arylindenes).

(6-tert-Butyl-5-methoxy-2-methyl-4-phenyl-1H-inden-1-yl)[4-(4-tert-butylphenyl)-2-methyl-1H-inden-1-yl]dimethylsilane

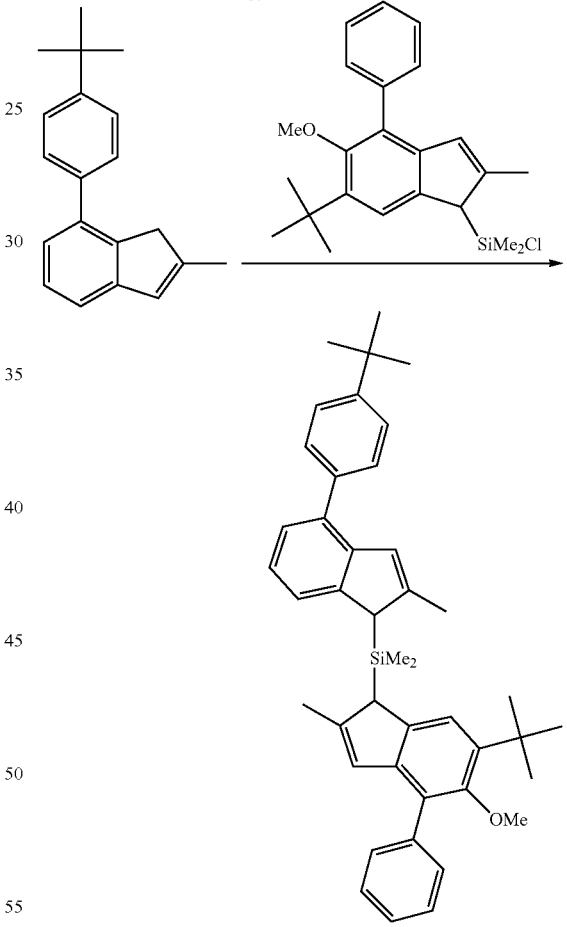

To a solution of 11.5 g (43.8 mmol) of 7-(4-tert-butyl-phenyl)-2-methyl-1H-indene in 300 ml of ether, 17.0 ml (42.5 mmol) of 2.5 M $^n$BuLi in hexanes was added in one portion at −78° C. This mixture was stirred overnight at room temperature, then cooled to −60° C., and 150 mg of CuCN was added. The resulting mixture was stirred for 1 h at −20° C., then cooled to −70° C., and 16.2 g of (6-tert-butyl-5-methoxy-2-methyl-4-phenyl-1H-inden-1-yl)(chloro)-dimethylsilane (42.08 mmol) in 150 ml of ether was added. Further on, this mixture was stirred overnight at ambient temperature, then 0.5 ml of water was added. This solution was filtered through a pad of silica gel 60 (40-63 um) which was additionally washed by dichloromethane. The combined organic elute was evaporated to dryness, and the obtained yellowish oil was purified by flash chromatography on silica gel 60 (40-63 um; eluent: hexane-dichloromethane, from 10:1 to 3:1, vol.). This procedure gave 23.4 g (91%) of the title compound as yellowish glass.

Anal. Calcd. for $C_{43}H_{50}OSi$: C, 84.54; H, 8.25%. Found: C, 84.70; H, 8.33%.

$^1$H NMR (CDCl$_3$): δ 7.59-7.18 (m), 6.89 (m), 6.83 (m), 6.51 (m), 6.48 (m), 3.77 (m), 3.73 (m), 3.68-3.70 (m), 3.31 (s), 3.29 (s), 2.25 (s), 2.23 (s), 2.16 (s), 2.10 (s), 1.50 (s), 1.48 (s), 1.45 (s), 1.44 (s), 0.00 (s), −0.09 (s), −0.11 (s), −0.12 (s).

Anti- and syn-dimethylsilylene(2-methyl-4-phenyl-5-methoxy-6-tert-butyl-indenyl)(2-methyl-4-(4-tert-butyl-phenyl)indenyl)zirconium dichloride

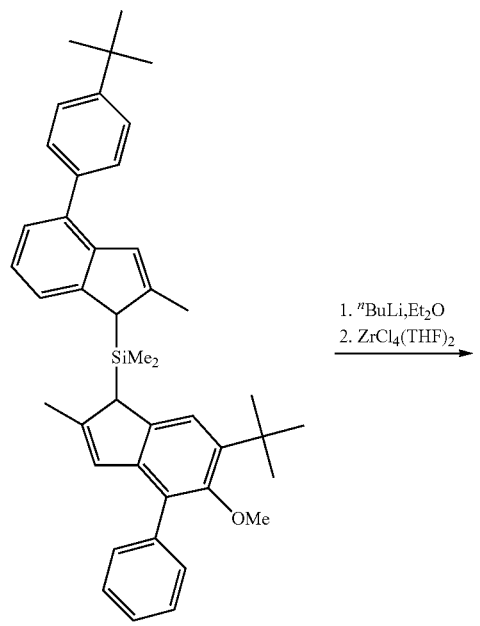

To a solution of 15.3 g (25.0 mmol) of (6-tert-butyl-5-methoxy-2-methyl-4-phenyl-1H-inden-1-yl)[4-(4-tert-butylphenyl)-2-methyl-1H-inden-1-yl]dimethylsilane in 300 ml of ether cooled to −78° C., 20.0 ml (50.0 mmol) of 2.5 M $^n$BuLi in hexanes was added in one portion. This mixture was stirred overnight at room temperature, then cooled to −60° C., and 9.43 g (25.0 mmol) of ZrCl$_4$(THF)$_2$ was added. The resulting mixture was stirred for 24 h (a light orange solution with a significant amount of precipitate was formed), then evaporated to dryness, and 350 ml of toluene was added. The resulting solution warmed to 80° C. was filtered through glass frit (G4) to form on the evidence of NMR spectroscopy a ca. 1 to 1 mixture of anti- and syn-zirconocenes. Crystals precipitated overnight from this solution at room temperature were collected, washed by 2×10 ml of cold toluene, and dried in vacuum. This procedure gave 3.50 g of pure syn-zirconocene as a light-orange microcrystalline powder. The mother liquor was evaporated to ca. 100 ml. Crystals precipitated overnight from this solution at room temperature were collected, washed with 10 ml of cold toluene, and dried in vacuum. This procedure gave additional amount (4.10 g) of pure syn-zirconocene. Thus, the combined yield of pure syn-zirconocene was 7.60 g (39%) as a light-orange microcrystalline powder. Crystals precipitated after 3 days at room temperature were collected, washed by 10 ml of cold toluene, and dried in vacuum. This procedure gave 2.95 g of pure anti-zirconocene as a slightly orange microcrystalline powder. Additional amount of this product was obtained in a similar manner from mother liquor evaporated to ca. 35 ml. Thus, the combined yield of anti-zirconocene was 5.65 g (29%).

Anti-E2

Anal. Calcd. for $C_{43}H_{48}Cl_2OSiZr$: C, 66.98; H, 6.27%. Found: C, 67.00; H, 6.31%.

$^1$H NMR (CDCl$_3$): δ 7.61-7.63 (m, 3H, 2,6-H in $C_6H_4$ and 5-H in indenyl of I), 7.54 (s, 1H, 7-H in indenyl of II), 7.46-7.48 (m, 2H, 3,5-H in $C_6H_4$ of I), 7.42 (m, 2H, 3,5-H in Ph of II), 7.37 (d, J=7.1 Hz, 1H, 7-H in indenyl of I), 7.32 (m, 1H, 4-H in Ph of II), 7.09 (dd, J=8.6 Hz, J=7.1 Hz, 1H, 6-H in indenyl of I), 7.02 (s, 1H, 3-H in indenyl of II), 6.57 (s, 1H, 3-H in indenyl of I), 3.39 (s, 3H, OMe), 2.25 (s, 3H, 2-Me in I), 2.17 (s, 3H, 2-Me in II), 1.39 (s, 9H, 6-$^t$Bu in II), 1.33 (s, 9H, 4-$^t$Bu in I), 1.31 (s, 6H, SiMe$_2$); where I is 4-(4-tert-butylphenyl)-2-methyl-1H-inden-1-yl, II—6-tert-butyl-5-methoxy-2-methyl-4-phenyl-1H-inden-1-yl.

Syn-E2

Anal. Found: C, 66.12; H, 6.35%.

$^1$H NMR (CDCl$_3$): δ 7.64 (m, 1H, 5-H in indenyl of I), 7.56-7.58 (m, 2H, 2,6-H in $C_6H_4$ of I), 7.54 (s, 1H, 7-H in indenyl of II), 7.44-7.46 (m, 2H, 3,5-H in $C_6H_4$ of I), 7.41 (m, 2H, 3,5-H in Ph of II), 7.30 (m, 1H, 4-H in Ph of II), 7.15 (d, J=7.1 Hz, 1H, 7-H in indenyl of I), 6.91 (s, 1H, 3-H in indenyl of II), 6.87 (dd, J=8.6 Hz, J=7.1 Hz, 1H, 6-H in indenyl of I), 6.47 (s, 1H, 3-H in indenyl of I), 3.20 (s, 3H, OMe), 2.44 (s, 3H, 2-Me in I), 2.37 (s, 3H, 2-Me in II), 1.44 (s, 3H, SiMeMe'), 1.34 (s, 9H, 6-$^t$Bu in II), 1.33 (s, 9H, 4-$^t$Bu in I), 1.22 (s, 3H, SiMeMe'); where I is 4-(4-tert-butylphenyl)-2-methyl-1H-inden-1-yl, II—6-tert-butyl-5-methoxy-2-methyl-4-phenyl-1H-inden-1-yl.

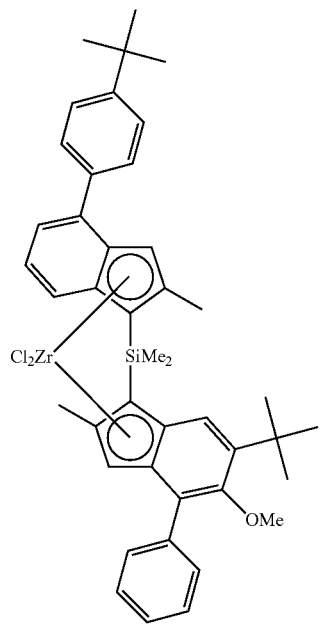

Synthesis of anti-dimethylsilylene(2-methyl-4-phenyl-5-methoxy-6-tert-butyl-indenyl)(2-methyl-4-(3,5-di-tert-butyl-phenyl)-6-tert-butyl-indenyl)zirconium dichloride Metallocene E3

4/7-Bromo-2-methyl-6/5-tert-butyl-1H-indene

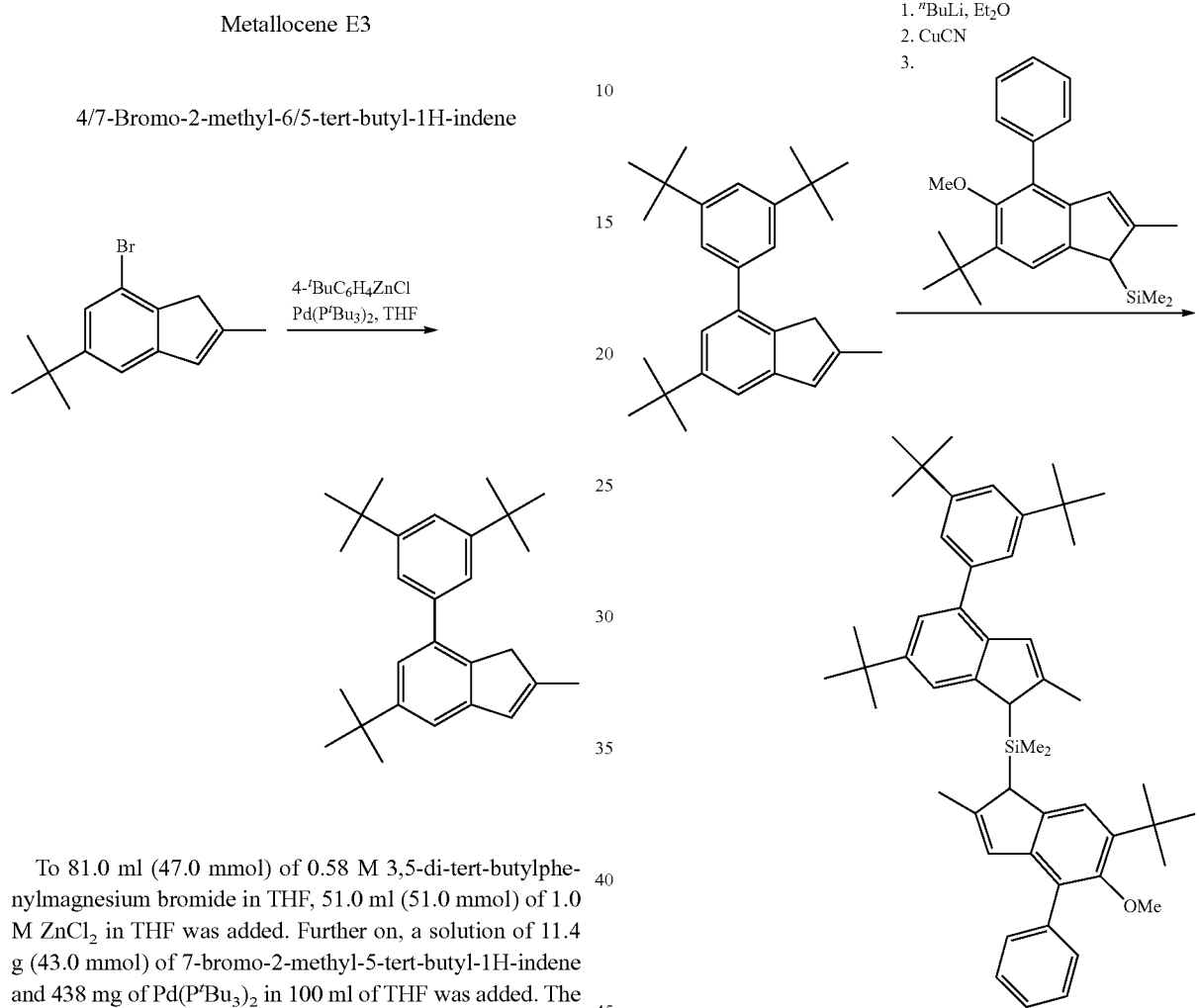

[6-tert-Butyl-4-(3,5-di-tert-butylphenyl)-2-methyl-1H-inden-1-yl]-(6-tert-butyl-5-methoxy-2-methyl-4-phenyl-1H-inden-1-yl)dimethylsilane To 81.0 ml (47.0 mmol) of 0.58 M 3,5-di-tert-butylphenylmagnesium bromide in THF, 51.0 ml (51.0 mmol) of 1.0 M ZnCl$_2$ in THF was added. Further on, a solution of 11.4 g (43.0 mmol) of 7-bromo-2-methyl-5-tert-butyl-1H-indene and 438 mg of Pd(P$^t$Bu$_3$)$_2$ in 100 ml of THF was added. The resulting mixture was stirred overnight at 65° C., then cooled to room temperature and, finally, poured into 200 ml of water. The organic layer was separated, and the aqueous layer was extracted with 3×100 ml of ethyl acetate. The combined organic extract was washed with 2×100 ml of cold water, dried over Na$_2$SO$_4$, and evaporated to dryness. The residue was distilled in vacuum using Kugelrohr apparatus.

This procedure gave 12.0 g (74%) of white crystalline solid.

Anal. Calcd. for C$_{28}$H$_{38}$: C, 89.78; H, 10.22%. Found: C, 89.69; H, 10.29%.

$^1$H NMR (CDCl$_3$): δ 7.42 (m), 7.38 (m), 7.35 (m), 7.30-7.32 (m), 7.19 (m), 6.59 (m, 3-H in indenyl), 6.62 (m, 3-H in indenyl), 3.36 (m, 1,1-H in indenyl), 3.33 (m, 1,1-H in indenyl), 2.13 (s, 2-Me in indenyl), 1.38-1.39 (s, 27H, $^t$Bu).

To a solution of 11.1 g (29.6 mmol) of 4/7-bromo-2-methyl-6/5-tert-butyl-1H-indene in 250 ml of ether, 11.9 ml (29.8 mmol) of 2.5 M $^n$BuLi in hexanes was added in one portion at −78° C. This mixture was stirred overnight at room temperature, then cooled to −60° C., and 150 mg of CuCN was added. The resulting mixture was stirred for 1 h at −20° C., and then a solution of 11.4 g (29.6 mmol) of (6-tert-butyl-5-methoxy-2-methyl-4-phenyl-1H-inden-1-yl)(chloro)-dimethylsilane in 200 ml of ether was quickly added at −70° C. The reaction mixture was allowed to warm to room temperature and stirred overnight, then treated with 0.5 ml of water, filtered through a short pad of silica gel 60 (40-63 um). The silica gel layer was additionally washed by 100 ml of dichloromethane. The combined elute was evaporated to dryness giving a yellowish oil which was purified by flash chromatography on silica gel 60 (4-63 μm; eluent: hexanes-dichloromethane from 10:1 to 3:1, vol.). This procedure gave 15.2 g (71%) of the title product as yellowish glassy solid.

Anal. Calcd. for C$_{51}$H$_{66}$OSi: C, 84.70; H, 9.20%. Found: C, 84.92; H, 9.34%.

$^1$H NMR (CDCl$_3$): δ 7.42-7.70 (m), 6.85 (s), 6.57 (s), 6.53 (s), 3.84 (m), 3.80 (m), 3.77 (m), 3.34 (s), 1.54 (s), 1.53 (s), 1.51 (s), 1.50 (s), 1.49 (s), 1.48 (s), −0.04 (s), −0.06 (s), −0.10 (s), −0.11 (s).

Complexes anti- and syn-dimethylsilanediyl[2-methyl-4-(3,5-di-tert-butylphenyl)-6-tert-butyl-inden-1-yl](2-methyl-4-phenyl-5-methoxy-6-tert-butyl-1H-inden-1-yl)zirconium dichloride

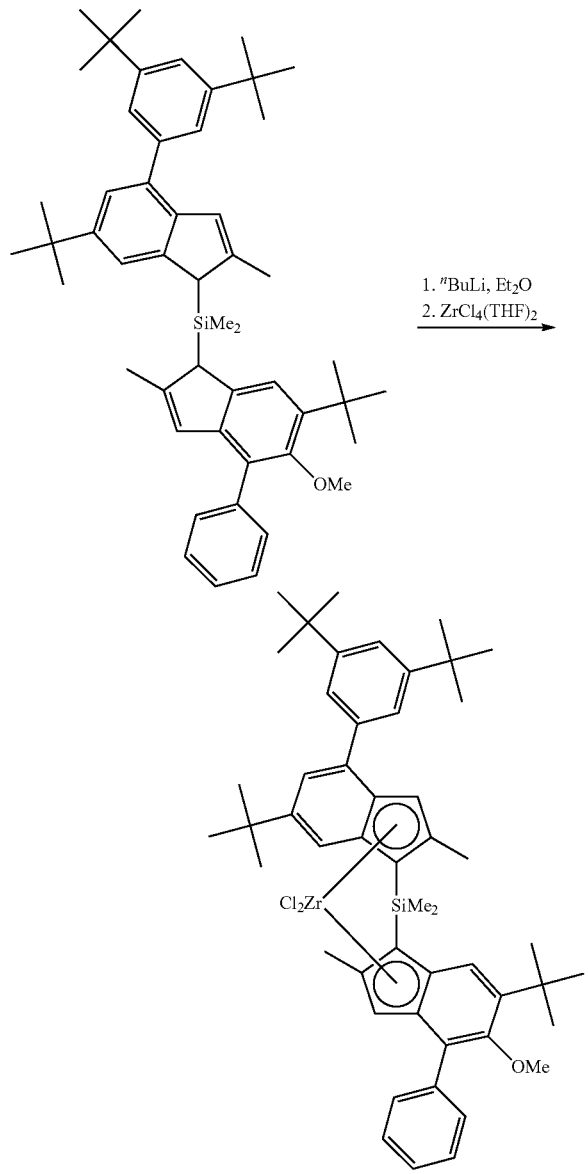

To a solution of 15.0 g (20.7 mmol) of [6-tert-butyl-4-(3,5-di-tert-butylphenyl)-2-methyl-1H-inden-1-yl] (6-tert-butyl-5-methoxy-2-methyl-4-phenyl-1H-inden-1-yl)dimethylsilane in 200 ml of ether cooled to −78° C., 16.5 ml (41.3 mmol) of 2.5 M $^n$BuLi in hexanes was added in one portion. This mixture was stirred overnight at room temperature, then cooled to −78° C., and 7.80 g (20.7 mmol) of ZrCl$_4$(THF)$_2$ was added. The resulting mixture was stirred for 24 h (a light orange solution with a significant amount of precipitate was formed), then evaporated to dryness, and 350 ml of toluene was added. The resulting mixture warmed to 80° C. was filtered through glass frit (G4). On the evidence of NMR spectroscopy, this mixture contained anti- and syn-zirconocenes in a ratio of ca. 70:30. The filtrate was evaporated to 100 ml, warmed to 80° C., and 25 ml of n-octane was added. Crystals precipitated after 24 h at −30° C. were collected, washed by 2×10 ml of a ca. 1 to 1 (vol.) mixture of toluene and n-hexane, and dried in vacuum. This procedure gave 6.62 g (36%) of pure anti-zirconocene as a light-orange crystalline powder. The mother liquor was evaporated to 50 ml, diluted with 100 ml of n-hexane, and crystallized overnight at −30° C. The formed precipitate was filtered through glass frit (G3) and then dried in vacuum. This procedure gave 6.40 g of a mixture of anti- and syn-zirconocene in the ratio of 3:2. The mother liquor was evaporated to dryness, and the residue was dissolved in 20 ml of hot n-octane. Crystals precipitated at −30° C. were collected, washed by 2×5 ml of cold n-hexane, and dried in vacuum. This procedure gave additional amount (450 mg) of pure anti-zirconocene. A precipitate formed after keeping a mother liquor at room temperature for 3 days was filtered off (G3), and then dried in vacuum. This procedure gave 210 mg of pure syn-zirconocene.

Anti-E3

Anal. Calcd. for C$_{51}$H$_{64}$Cl$_2$OSiZr: C, 69.35; H, 7.30%. Found: C, 69.43; H, 7.41%.

$^1$H NMR (CDCl$_3$): δ 7.15-7.60 (m, 11H, 5,7-H in indenyl and 2,4,6-H in aryl of I as well as 7-H in indenyl and Ph in II), 6.87 (s, 1H, 3-H in indenyl of I), 6.53 (s, 1H, 3-H in indenyl of II), 3.40 (s, 3H, OMe), 2.22 (s, 3H, 2-Me in indenyl), 2.20 (s, 3H, 2-Me in indenyl), 1.40 (s, 9H, 6-$^t$Bu in indenyl of I), 1.36 (s, 18H, 3,5-$^t$Bu in aryl), 1.33 (s, 9H, 6-$^t$Bu in indenyl of II), 1.32 (s, 3H, SiMeMe'), 1.30 (s, 3H, SiMeMe'), where I is 6-tert-butyl-4-(3,5-di-tert-butylphenyl)-2-methyl-1H-inden-1-yl, II—6-tert-butyl-5-methoxy-2-methyl-4-phenyl-1H-inden-1-yl.

Syn-E3

Anal. Found: C, 69.47; H, 7.40%.

$^1$H NMR (CDCl$_3$): δ 7.16-7.54 (m, 11H, 5,7-H in indenyl and 2,4,6-H in aryl of I as well as 7-H in indenyl and Ph in II), 6.88 (s, 1H, 3-H in indenyl of I), 6.53 (s, 1H, 3-H in indenyl of II), 3.17 (s, 3H, OMe), 2.45 (s, 3H, 2-Me in indenyl), 2.40 (s, 3H, 2-Me in indenyl), 1.45 (s, 3H, SiMeMe'), 1.38 (s, 18H, 3,5-$^t$Bu in aryl), 1.35 (s, 9H, 6-$^t$Bu in indenyl of I), 1.31 (s, 9H, 6-$^t$Bu in indenyl of II), 1.21 (s, 3H, SiMeMe'), where I is 6-tert-butyl-4-(3,5-di-tert-butylphenyl)-2-methyl-1H-inden-1-yl, II—6-tert-butyl-5-methoxy-2-methyl-4-phenyl-1H-inden-1-yl.

Preparation of the Solid Catalysts

Catalyst E1:

Inside the glovebox, 80 μL of a dry and degassed mixture of perfluoroalkylethyl acrylate ester were mixed in a septum vial with 2 mL of a 30 wt-% solution of MAO in toluene and left to react overnight. The following day, 58.9 mg of the metallocene E1 of the invention (rac-anti-Me$_2$Si(2-Me-4-Ph-6-tBu-Ind)(2-Me-4-Ph-5-OMe-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.62 g (catalyst E1) of a red free flowing powder was obtained.

Catalyst E2:

Inside the glovebox, 80 µL of a dry and degassed mixture of perfluoroalkylethyl acrylate ester were mixed in a septum vial with 2 mL of a 30 wt-% solution of MAO in toluene and left to react overnight. The following day, 58.7 mg of the metallocene E2 of the invention (rac-anti-Me$_2$Si(2-Me-4-(p-tBuPh)-Ind)(2-Me-4-Ph-5-OMe-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.52 g (catalyst E2) of a red free flowing powder was obtained.

Catalyst E3:

Inside the glovebox, 80 µL of a dry and degassed mixture of perfluoroalkylethyl acrylate ester were mixed in a septum vial with 2 mL of a 30 wt-% solution of MAO in toluene and left to react overnight. The following day, 67.1 mg of the metallocene E3 of the invention (rac-anti-Me$_2$Si(2-Me-4-(3,5-di-tBuPh)-6-tBu-Ind)(2-Me-4-Ph-5-OMe-6-tBu-Ind)ZrCl$_2$) (0.076 mmol, 1 equivalent) were dissolved with 4 mL of the MAO solution in another septum bottle and left to stir inside the glovebox. After 60 minutes, the 4 mL of the MAO-metallocene solution and 1 mL of the perfluoroalkylethyl acrylate ester mixture in MAO solution were successively added into a 50 mL emulsification glass reactor containing 40 mL of hexadecafluoro-1,3-dimethylcyclohexane kept at −10° C. and equipped with an overhead stirrer (stirring speed=600 rpm). Total amount of MAO is 5 mL (300 equivalents). A red emulsion formed immediately and was stirred during 15 minutes at 0° C./600 rpm. Then the emulsion was transferred via a 2/4 teflon tube to 100 mL of hot hexadecafluoro-1,3-dimethylcyclohexane heated to 90° C., and stirred at 600 rpm until the transfer is completed. The speed was reduced to 300 rpm. After 15 minutes stirring, the oil bath was removed and the stirrer turned off. The catalyst was left to settle up on top of the hexadecafluoro-1,3-dimethylcyclohexane and after 35 minutes the solvent was siphoned off. The remaining red catalyst was dried during 2 hours at 50° C. over an argon flow. 0.67 g (catalyst E3) of a red free flowing powder was obtained.

Comparative Catalyst C1

Comparative example catalyst C1 was synthesized according to the above described recipe with 78.2 mg of rac-methyl(cyclohexyl)silanediylbis[2-methyl-4-(4-tert-butylphenyl)indenyl]zirconium dichloride as the metallocene.

Comparative Example C2

Comparative example catalyst C2 was prepared according to the example E1 of WO2012/001052 using rac-1,1'-dimethylsilylene-bis[2-isobutyl-4-(4-tert-butylphenyl)-5,6,7-trihydro-s-indacen-1-yl]zirconium dichloride as the metallocene.

Comparative Example C3

C-3a is the commercial product Borsoft SA233CF commercially available from Borealis AG, a random-heterophasic copolymer having an MFR (230° C./2.16 kg) of 0.8 g/10 min. C-3b is the commercial product BEC5012 commercially available from Borealis AG, a heterophasic copolymer for non-pressure pipes having an MFR (230° C./2.16 kg) of 0.3 g/10 min.

TABLE 1

| Catalyst composition as determined by ICP | | | |
|---|---|---|---|
| Cat. | Al (%) | Zr (%) | Al/Zr (molar) |
| E1 | 26.20 | 0.31 | 285 |
| E2 | 18.90 | 0.24 | 266 |
| E3 | 26.10 | 0.32 | 276 |
| C1 | 31.00 | 0.37 | 283 |

E1P, E2P, E3P and C1P: Off-Line Prepolymerization of Catalysts E1, E2, E3 and C1

The catalysts of the invention E1, E2 and E3 as well comparative catalyst C1 were pre-polymerised according to the following procedure: off-line pre-polymerisation experiments were done in a 125 mL pressure reactor equipped with gas-feeding lines and an overhead stirrer. Dry and degassed hexadecafluoro-1,3-dimethylcyclohexane (15 mL) and the desired amount of the red catalyst to be pre-polymerised were loaded into the reactor inside a glovebox and the reactor was sealed. The reactor was then taken out from the glovebox and placed inside a water cooled bath. The overhead stirrer and the feeding lines were then connected. The feeding line was pressurized with hydrogen, and the experiment was started by opening the valve between the H$_2$ feed line and the reactor. At the same time propylene feed was started through the same H$_2$ feeding line in order to ensure that all the hydrogen would be fed into the reactor. The propylene feed was left open, and the monomer consumption was compensated by keeping the total pressure in the reactor constant (about 5 barg). The experiment was continued until a polymerisation time sufficient to provide the desired degree of polymerisation. The reactor was then taken back inside the glovebox before opening and the content was poured into a glass vessel. The hexadecafluoro-1,3-dimethylcyclohexane was evaporated until a constant weight was obtained to yield a pre-polymerised pink catalyst. The degree of polymerisation was determined gravimetrically and/or by analysis of the ash and/or aluminium content of the catalyst to be 3.5 for E1P, 4.6 for E2P, 2.9 for E3P and 3.1 for C1P.

C2P: Off-Line Prepolymerization of Catalyst C2

The solid catalyst C2 was further prepolymerised according to the following procedure. The catalyst was off-line prepolymerised according to the following procedure: off-line pre-polymerisation experiments were done in a 125 mL pressure reactor equipped with gas-feeding lines and an overhead stirrer. Dry and degassed perfluoro-1,3-dimethyl-cyclohexane (15 cm$^3$) and the desired amount of the red catalyst to be pre-polymerised were loaded into the reactor inside a glovebox and the reactor was sealed. The reactor was then taken out from the glovebox and placed inside a water cooled bath. The overhead stirrer and the feeding lines were then connected. The feeding line was pressurized with hydrogen, and the experiment was started by opening the valve between the hydrogen feed line and the reactor. At the same time propylene feed was started through the same hydrogen feeding line in order to ensure that all the hydrogen would be fed into the reactor. The propylene feed was left open, and the monomer consumption was compensated by keeping the total pressure in the reactor constant (about 5 barg). The experiment was continued until a polymerisation time sufficient to provide the desired degree of polymerisation. The reactor was then taken back inside the glovebox before opening and the content was poured into a glass vessel. The perfluoro-1,3-dimethylcyclohexane was evaporated until a constant weight was obtained to yield a pre-polymerised pink catalyst. The prepolymerisation degree (weight of polymer matrix/weight of solid catalyst before prepolymerisation step) was determined gravimetrically and/or by analysis of the ash and/or aluminium content of the catalyst.

Polymerisations:

Heterophasic Ethylene-Propylene Copolymerization with Catalyst E1P.

Heterophasic copolymer was prepared with catalyst E1P in a sequential bulk/gas phase process as follows: A 21.2 L autoclave with double helix stirrer containing ~0.4 barg propylene was filled with additional 5.18 kg propylene. After adding 0.2 NL H$_2$ and 0.97 mmol triethylaluminium (1 molar solution in hexane) using a stream of 248 g propylene, the solution was stirred at 250 rpm. After 20 min the reactor temperature was increased to 40° C. and 298 mg of the solid, pre-polymerized catalyst E1P was contacted with 5 ml perfluoro-1,3-dimethylcyclohexane under N$_2$ pressure (0.003 mol at ~10 barg) in a stainless-steel vial connected to the autoclave for 60 sec and flushed into the reactor with 494 g propylene. After that the stirring speed was increased to 350 rpm and the temperature in the reactor increased to 70° C. over ~13 min. This temperature was held for 30 min after achieving 68° C. After that the pressure was decreased to 1 bar-a via flashing. To achieve target conditions for gas phase of 15 bar-g at 60° C., ethylene and propylene are dosed in a ratio of C3/C2=1.26 g/g into the reactor until a total amount of 429 g over 8 min. 60° C. (temperature decreased during flashing because of vaporization enthalpy) was achieved 16 min after start of pressure increase and the total pressure was constantly held at 15 bar-g via dosing ethylene and propylene in a ratio of C3/C2=1.83 g/g. The polymerisation was stopped 67 min after start of pressure increase to 15 barg via flashing and cooling. The residence time used for calculation of catalyst activity in gas phase was 55.5 min (start after achieving of polymerisation temperature of 58° C. in gas phase).

After 3 times spilling the reactor with N$_2$ and one vacuum/N$_2$ cycle the product was taken out and dried overnight in a hood and additionally 2 hours in a vacuum drying oven at 60° C.

Heterophasic Ethylene-Propylene Copolymerization with Catalyst E2P

Heterophasic copolymer was prepared with catalyst E2P in a sequential bulk/gas phase process as follows: A 21.2 L autoclave with double helix stirrer containing ~0.5 barg propylene was filled with additional 3.97 kg propylene. After adding 0.2 NL hydrogen and 0.73 mmol triethylaluminium (1 molar solution in hexane) using a stream of 246 g propylene the solution was stirred at 250 rpm. After 20 min the reactor temperature was increased to 40° C. and 253 mg of the solid, pre-polymerized catalyst E2P (degree of polymerisation 4.6) was contacted with 5 ml perfluoro-1,3-dimethylcyclohexane under nitrogen-pressure (0.003 mol at ~10 bar-g) for 60 sec and spilled into the reactor with 243 g propylene. After that the stirring speed was increased to 350 rpm and the temperature in the reactor increased to 70° C. over ~17 min. This temperature was held for 30 mins after achieving 68° C. After that the pressure was decreased to 1.1 barg via flashing. To achieve target conditions for gas phase of ~15 barg at 60° C., ethylene and propylene are dosed in a ratio of C3/C2=1.23 g/g into the reactor until a total amount of 406 g over 8 min. 60° C. (temperature decreased during flashing because of vaporization enthalpy) was achieved 14 min after start of pressure increase and the total pressure was constantly held at 15 barg via dosing ethylene and propylene in a ratio of C3/C2=1.83 g/g. The polymerisation was stopped 41.5 min after start of pressure increase to 15 barg via flashing and cooling. The residence time used for calculation of catalyst activity in gas phase was 27.5 min (start after achieving of polymerisation temperature of 58° C. in gas phase).

After 3 times spilling the reactor with nitrogen and one vacuum/nitrogen cycle the product is taken out and dried overnight in a hood and additionally 2 hours in a vacuum drying oven at 60° C.

This polymerisation was repeated using different amount of catalyst and C3/C2 feeds.

Heterophasic Ethylene-Propylene Copolymerization with Catalyst E3P.

Heterophasic copolymer was prepared with catalyst E3P in a sequential bulk/gas phase process as follows: A 21.2 L autoclave with double helix stirrer containing ~0.5 barg propylene was filled with additional 3.96 kg propylene. After adding 0.2 NL hydrogen and 0.73 mmol triethylaluminium (1 molar solution in hexane) using a stream of 247 g propylene the solution was stirred at 250 rpm. After 20 min the reactor temperature was increased to 40° C. and 212 mg of the solid, pre-polymerized catalyst E3P (degree of polymerisation 2.9) was contacted with 5 ml perfluoro-1,3-dimethylcyclohexane under nitrogen-pressure (0.003 mol at ~10 bar-g) for 60 sec and spilled into the reactor with 242 g propylene. After that the stirring speed was increased to 350 rpm and the temperature in the reactor increased to 70° C. over ~15 min. This temperature was held for 30 mins after achieving 68° C. After that the pressure was decreased to 0.9 bara via flashing. To achieve target conditions for gas phase of ~15 barg at 60° C., ethylene and propylene are dosed in a ratio of C3/C2=0.4 g/g into the reactor until a total amount of 351 g over 8 min. 60° C. (temperature decreased during flashing because of vaporization enthalpy) was achieved 18 min after start of pressure increase and the total pressure was constantly held at 15 barg via dosing ethylene and propylene in a ratio of C3/C2=1 g/g. The polymerisation was stopped 93 min after start of pressure increase to 15 barg via flashing and cooling. The residence time used for calculation of catalyst activity in gas phase was 82 min (start after achieving of polymerisation temperature of 58° C. in gas phase).

After 3 times spilling the reactor with nitrogen and one vacuum/nitrogen cycle the product is taken out and dried overnight in a hood and additionally 2 hours in a vacuum drying oven at 60° C.

Heterophasic Ethylene-Propylene Copolymerisation with C1P (Comparative)

Batch production of a heterophasic ethylene copolymer with pre-polymerized comparison catalyst C1P in bulk/gas phase process: A stirred autoclave (double helix stirrer) with a volume of 21.2 dm$^3$ containing ~0.5 barg propylene was filled with additional 5.18 kg propylene. After adding 0.2 In hydrogen and 0.97 mmol triethylaluminium (1 molar solution in hexane) using a stream of 244 g propylene the solution was stirred at 250 rpm. After 20 min the reactor temperature was increased to 40° C. and 494 mg of the solid, pre-polymerized catalyst C1P was contacted with 5 ml perfluoro-1,3-dimethylcyclohexane under nitrogen pressure (0.003 mol at ~10 barg) for 60 sec and spilled into the reactor with 491 g propylene. After that the stirring speed was increased to 350 rpm and the temperature in the reactor increased to 70° C. over ~17 min. This temperature was held for 30 min after achieving 68° C. After that the pressure is decreased to 1.1 barg via flashing. To achieve target conditions for gas phase of 15 barg at 60° C. ethylene and propylene are dosed in a ratio of C3/C2=1.23 g/g into the reactor until a total amount of 401 g over 8 min. 60° C. (temperature decreased during flashing because of vaporization enthalpy) was achieved 19 min after start of pressure increase and the total pressure was constantly held at 15 barg via dosing ethylene and propylene in a ratio of C3/C2=1.83 g/g. The polymerisation was stopped 103 min after start of pressure increase to 15 barg via flashing and cooling. The residence time used for calculation of catalyst activity in gas phase was 90 min (start after achieving of polymerisation temperature of 58° C. in gas phase).

After 3 times spilling the reactor with nitrogen and one vacuum/nitrogen cycle the product was taken out and dried over night in a hood and additionally 2 hours in a vacuum drying oven at 60° C.

Catalyst activity for E1P and E2P and E3P was determined according to:

Activity kg/g(cat)/h={amount of polymer produced in kg/[(prepolymerized catalyst loading in grams)×polymerization time in hours]}×(1+ prepolymerization degree).

Heterophasic Ethylene-Propylene Copolymerisation with C2P (Ex A) (Comparative)

A stirred autoclave (double helix stirrer) with a volume of 21.2 dm$^3$ containing ~0.4 barg propylene was filled with additional 3.97 kg propylene. After adding 0.4 NL hydrogen and 1.83 mmol triethylaluminium (1 molar solution in hexane) using a stream of 245 g propylene the solution was stirred at 250 rpm. After 20 min the reactor temperature was increased to 40° C. and 65 mg of the solid, pre-polymerized catalyst C2P (degree of polymerisation 3.9) was contacted with 5 ml perfluoro-1,3-dimethylcyclohexane under nitrogen-pressure (0.003 mol at ~10 barg) for 60 sec and spilled into the reactor with 244 g propylene. After that the stirring speed is increased to 350 rpm and the temperature in the reactor held at 40° C. for 15 min (pre-polymerisation). Then the temperature is increased to 70° C. over ~16 min and 1.17 NL hydrogen added during this period. This temperature is held for 30 min after achieving 68° C. After that the pressure was decreased to 1.3 barg via flashing. To achieve target conditions for gas phase of 15 barg at 60° C., ethylene and propylene were dosed in a ratio of C3/C2=1.22 [g/g] into the reactor until a total amount of 421 g over 7.5 min. Achieving 60° C. (temperature decreased during flashing because of vaporization enthalpy) 16 min after start of pressure increase the total pressure was constantly held at 15 barg via dosing ethylene and propylene in a ratio of C3/C2=1.83 [g/g]. The polymerisation has been stopped 149 min after pressure increase to 15 barg via flashing and cooling.

After 3 times spilling the reactor with nitrogen and one vacuum/nitrogen cycle the product was taken out and dried over night in a hood and additionally 2 hours in a vacuum drying oven at 60° C.

Heterophasic Ethylene-Propylene Copolymerisation with C2P (Ex B) (Comparative)

A stirred autoclave (double helix stirrer) with a volume of 21.2 dm$^3$ containing ~0.4 barg propylene was filled with additional 3.97 kg propylene. After adding 0.4 NL H$_2$ and 0.73 mmol triethylaluminium (1 molar solution in hexane) using a stream of 244 g propylene the solution was stirred at 250 rpm. After 20 min 64 mg of the solid, pre-polymerized catalyst C2P (degree of polymerisation 3.9) was contacted with 5 ml perfluoro-1,3-dimethylcyclohexane under nitrogen-pressure (0.003 mol at ~10 barg) for 60 sec and spilled into the reactor with 242 g propylene at a stirring speed of 350 rpm. The temperature in the reactor was held at 20° C. for 10 min (pre-polymerisation). Then the temperature was increased to 70° C. over ~23 min and 0.6 NL H$_2$ are added during this period. This temperature was held for 30 min after achieving 68° C. After that the pressure was decreased to 1.2 barg via flashing. To achieve target conditions for gas phase of 25 barg at 80° C., ethylene and propylene were dosed in a ratio of C3/C2=1.86 [g/g] into the reactor until a total amount of 799 g was present over 7.2 min. Achieving 80° C. (temperature decreased during flashing because of vaporization enthalpy) 14 min after start of pressure increase the total pressure was constantly held at 25 barg via dosing ethylene and propylene in a ratio of C3/C2=2.48 g/g. The polymerisation was stopped 138 min after pressure increase to 25 barg via flashing and cooling.

After 3 times spilling the reactor with nitrogen and one vacuum/N$_2$ cycle the product was taken out and dried over night in a hood and additionally 2 hours in a vacuum drying oven at 60° C.

Results of heterophasic polymerisations are summarised in Tables 1 to 4.

TABLE 1

Heterophasic ethylene-propylene copolymerisations

| Ex | Cat. | Prepoly'd Catalyst amount (mg) | Total polymer yield (g) | Polym Yield in bulk (g) | Activity in bulk kg$_{PP}$/g$_{cat}$/h | C3/C2 in feed (transition gas phase) (g/g) | C3/C2 in feed (gas phase) (g/g) | Residence time (gas phase) (min) | Polym Yield in gas phase) (g) | Activity in$^{(1)}$ gas phase kg/g$_{cat}$/h |
|---|---|---|---|---|---|---|---|---|---|---|
| c-1 | C1P | 494 | 915 | 601 | 10.0 | 1.23 | 1.83 | 90 | 314 | 1.74 |
| 1 | E1P | 298 | 1301 | 787 | 23.8 | 1.26 | 1.83 | 55.5 | 514 | 8.39 |

TABLE 1-continued

Heterophasic ethylene-propylene copolymerisations

| Ex | Cat. | Prepoly'd Catalyst amount (mg) | Total polymer yield (g) | Polym Yield in bulk (g) | Activity in bulk kg$_{PP}$/g$_{cat}$/h | C3/C2 in feed (transition gas phase) (g/g) | C3/C2 in feed (gas phase) (g/g) | Residence time (gas phase) (min) | Polym Yield in gas phase (g) | Activity in[1] gas phase kg/g$_{cat}$/h |
|---|---|---|---|---|---|---|---|---|---|---|
| 2 | E2P | 257 | 680 | 483 | 21.0 | 0.40 | 1.00 | 22.5 | 197 | 11.45 |
| 3 | E2P | 253 | 692 | 428 | 18.9 | 1.23 | 1.83 | 27.5 | 264 | 12.75 |
| 4 | E3P | 212 | 1100 | 762 | 28.0 | 0.4 | 1.00 | 82 | 338 | 4.6 |

[1]Activity in kg of polymer per gram of catalyst per hour
(MFR(XS) calculated from iV(XS) & C2(XS) based on Grein et al. Rheol.Acta 2007, MFR(Matrix) from logarithmic mixing rule);

TABLE 2

Heterophasic ethylene-propylene copolymerisations—polymer properties

| Ex | Cat. | MFR$_2$ (g/10 min) | C2 in XS (IR) wt % | XS wt-% | IV (XS) dL/g | G'23° C. MPa | Tg (EPR) | M$_w$ at the max of MWD curve of the C2C3 copolymer kg/mol | M$_w$ (XS) kg/mol |
|---|---|---|---|---|---|---|---|---|---|
| c-1 | C1P | 2.43 | 23.3 | 34.3 | 0.58 | 228 | −38.6 | 47 | 41 |
| 1 | E1P | 0.47 | 23 | 38 | 1.15 | 185 | −38 | 94 | 94 |
| 2 | E2P | 0.07 | 43.3 | 28.6 | 1.26 | 311 | −54 | 140 | 101 |
| 3 | E2P | 0.15 | 22.3 | 35 | 1.24 | 222 | −36 | 129 | 111 |
| 4 | E3P | 0.35 | 39.9 | 35.2 | 1.55 | 271 | −52 | 146 | 125 |
| C-2Pa | C-2P | 7.7 | 20.7 | 23.7 | 2.12 | 350 | | | |
| C-2Pb | C-2P | 0.5 | 18.5 | 31.4 | 3.67 | 306 | | | |
| C-3a | ZN | 0.8 | 30.5 | 28.7 | 2.34 | 277 | | | |
| C-3b | ZN | 0.3 | 63.2 | 12.0 | 2.8 | 552 | | | |

TABLE 3

| Ex | Tg(EPR) °C. | MFR(XS) g/10 min | MFR (Matrix) g/10 min | MFR(XS)/ MFR (Matrix) |
|---|---|---|---|---|
| c-1 | −38.6 | 110 | 0.32 | 331 |
| 1 | −38 | 65 | 0.023 | 2837 |
| 2 | −54 | 57 | 0.005 | 11932 |
| 3 | −36 | 48 | 0.007 | 7146 |
| 4 | −52 | 35 | 0.029 | 1220 |
| C-2Pa | −34 | 1.2 | 13.7 | 0.087 |
| C-2Pb | −33 | 0.08 | 1.16 | 0.069 |
| C-3a | −54 | 0.8 | 0.8 | 1 |
| C-3b | −65 | 0.6 | 0.27 | 2.20 |

For examples 1 and 4, an extended mechanical characterization has been done demonstrating an extremely low brittle-to-ductile transition temperature (BDTT) based on Charpy notched impact values (see FIG. 1).

The inventive examples show an extremely advantageous mechanical profile despite the low molecular weight of the EPR phase which is normally considered to be detrimental for impact strength. An additional comparison with two commercial copolymer grades based on Ziegler Natta catalysts (C-3a and C-3b) is summarized in Table 4 showing clearly the improved performance at −20° C.

TABLE 4

| Catalyst | MFR (Matrix) g/10 min | MFR (Total) g/10 min | IV (XS) dl/g | XS wt % | MFR(XS)/ MFR (Matrix) — | C2 (XS) wt % | BDTT °C. | Charpy NIS −20° C. kJ/m² | Charpy NIS 23° C. kJ/M² | Tensile Mod. MPa | Strain @ break % |
|---|---|---|---|---|---|---|---|---|---|---|---|
| C-2a | 13.7 | 7.7 | 2.12 | 23.7 | 0.087 | 20.7 | −7 | 4.9 | 49.0 | 882 | 345 |
| C-2b | 1.17 | 0.5 | 3.67 | 31.4 | 0.069 | 18.5 | −19 | 64.8 | 77.1 | 709 | 360 |
| 1 | 0.023 | 0.5 | 1.15 | 38.0 | 2837 | 23.5 | −33 | 107.6 | NB | 222 | 112 |
| 4 | 0.029 | 0.4 | 1.55 | 35.2 | 7146 | 39.9 | −34 | 112.3 | NB | 558 | 108 |
| C-3a | 0.8 | 0.8 | 2.34 | 28.7 | 1.0 | 30.5 | n.d. | 5.0 | 83.0 | 470 | 460 |
| C-3b | 0.26 | 0.3 | 2.80 | 12.0 | 2.2 | 63.2 | n.d. | 5.0 | 70.0 | 1295 | 450 |

The invention claimed is:

1. A heterophasic polypropylene resin comprising an asymmetrical metallocene-produced polypropylene homopolymer phase (A) and an asymmetrical metallocene-produced ethylene-propylene copolymer phase (B) dispersed within the phase (A), wherein the same asymmetrical metallocene catalyst is used to produce the phase (A) and the phase (B), and wherein the xylene soluble (XS) fraction of the heterophasic polypropylene resin is in the range 20 to less than 50 wt %;

the heterophasic polypropylene resin has an $MFR_2$ of 0.05 to 2 g/10 min;

the ethylene content of the xylene soluble fraction of the heterophasic polypropylene resin is in the range of at least 20 wt % to less than 50 wt %;

the $MFR_2$ (xylene insoluble) is 0.2 g/10 min or less;

the $MFR_2$ (XS)/$MFR_2$ (xylene insoluble) ≥350; and wherein the heterophasic polypropylene resin has a notched Charpy impact strength at −20° C. that is at least 75 kJ/m².

2. The heterophasic polypropylene resin of claim 1, wherein the $MFR_2$ (XS)/$MFR_2$(xylene insoluble)≥500.

3. The heterophasic polypropylene resin of claim 1, wherein the brittle-to-ductile transition temperature BDTT is less than −25° C.

4. The heterophasic polypropylene resin of claim 1, wherein the notched Charpy impact strength at −20° C. is at least 90 kJ/m².

5. The heterophasic polypropylene resin of claim 1, wherein the heterophasic polypropylene resin comprises 25 to 45 wt % XS content.

6. The heterophasic polypropylene resin of claim 1, having a tensile modulus of 50 to 800 MPa.

7. An article comprising the heterophasic polypropylene resin of claim 1.

8. A polymer blend comprising the heterophasic polypropylene copolymer as claimed in claim 1 and a second different polyolefin.

* * * * *